(12) United States Patent
Nolan et al.

(10) Patent No.: US 11,236,899 B2
(45) Date of Patent: Feb. 1, 2022

(54) LIGHTING MODULE WITH CUTOFF TUNING EFFECTS

(71) Applicant: M3 Innovation, LLC, Syracuse, NY (US)

(72) Inventors: Christopher D. Nolan, Camillus, NY (US); Joseph R. Casper, Baldwinsville, NY (US)

(73) Assignee: M3 Innovation, LLC, Syracuse, NY (US)

( * ) Notice: Subject to any disclaimer, the term of this patent is extended or adjusted under 35 U.S.C. 154(b) by 0 days.

(21) Appl. No.: 16/818,423

(22) Filed: Mar. 13, 2020

(65) Prior Publication Data

US 2021/0160977 A1    May 27, 2021

Related U.S. Application Data

(60) Provisional application No. 62/940,644, filed on Nov. 26, 2019.

(51) Int. Cl.
*F21V 21/002* (2006.01)
*F21V 21/14* (2006.01)
(Continued)

(52) U.S. Cl.
CPC ............... *F21V 29/76* (2015.01); *A61L 2/10* (2013.01); *A61L 2/24* (2013.01); *A61L 2/26* (2013.01);
(Continued)

(58) Field of Classification Search
CPC ...... H05B 45/10; H05B 47/155; H05B 47/19; H05B 45/37; H05B 47/20; H05B 45/42; H05B 45/44; H05B 47/165; A61L 2/10; A61L 2/24; A61L 2/26; A61L 2202/11; A61L 2202/14; A61L 2202/25; F21S 2/00;
(Continued)

(56) References Cited

U.S. PATENT DOCUMENTS 8,070,314 B2 * 12/2011 St. Ives ................. F21V 21/005
362/225
8,556,451 B1 * 10/2013 Wilkinson ............ F21V 21/005
362/217.05
(Continued)

FOREIGN PATENT DOCUMENTS

WO    WO-2019107606 A1 *  6/2019  .............. F21V 23/04

*Primary Examiner* — Borna Alaeddini
(74) *Attorney, Agent, or Firm* — Bond Schoeneck and King PLLC; David Nocilly

(57) ABSTRACT

An elongated lighting module having an asymmetric illumination source formed from at least two rows of light emitting diodes (LEDs) that extend along the long axis of the module and are independently controllable. The illumination source is rectangular and oriented so that the rows of LEDs extend along the long axis of the module. The module has couplings at each end that allow additional modules to be interconnected therewith using a linking member and a clamp. The lighting modules are powered via a wiring harness that extends down a support pole to a power converter stack having LED drivers to control the modules. The asymmetric illumination source may be driven to change the beam angle and cutoff of illumination by independently adjusting the rows of light emitting diodes of the lighting module.

7 Claims, 30 Drawing Sheets

(51) Int. Cl.
| | |
|---|---|
| F21V 23/00 | (2015.01) |
| F21Y 115/10 | (2016.01) |
| F21V 29/76 | (2015.01) |
| F21S 8/08 | (2006.01) |
| A61L 2/10 | (2006.01) |
| A61L 2/24 | (2006.01) |
| A61L 2/26 | (2006.01) |
| F21V 23/04 | (2006.01) |
| H05B 47/20 | (2020.01) |
| H05B 45/42 | (2020.01) |
| H05B 45/44 | (2020.01) |
| H05B 47/19 | (2020.01) |
| H05B 47/165 | (2020.01) |
| F21S 4/28 | (2016.01) |
| F21S 2/00 | (2016.01) |
| F21S 8/04 | (2006.01) |
| H01R 24/84 | (2011.01) |
| F21V 29/74 | (2015.01) |
| H05B 45/37 | (2020.01) |
| H05B 45/10 | (2020.01) |
| H05B 47/155 | (2020.01) |
| F21V 21/30 | (2006.01) |
| F21Y 105/16 | (2016.01) |
| F21W 131/105 | (2006.01) |

(52) U.S. Cl.
CPC .............. *F21S 2/00* (2013.01); *F21S 2/005* (2013.01); *F21S 4/28* (2016.01); *F21S 8/043* (2013.01); *F21S 8/085* (2013.01); *F21S 8/086* (2013.01); *F21V 21/002* (2013.01); *F21V 21/14* (2013.01); *F21V 21/30* (2013.01); *F21V 23/003* (2013.01); *F21V 23/008* (2013.01); *F21V 23/0435* (2013.01); *F21V 29/74* (2015.01); *H01R 24/84* (2013.01); *H05B 45/10* (2020.01); *H05B 45/37* (2020.01); *H05B 45/42* (2020.01); *H05B 45/44* (2020.01); *H05B 47/155* (2020.01); *H05B 47/165* (2020.01); *H05B 47/19* (2020.01); *H05B 47/20* (2020.01); *A61L 2202/11* (2013.01); *A61L 2202/14* (2013.01); *A61L 2202/25* (2013.01); *F21W 2131/105* (2013.01); *F21Y 2105/16* (2016.08); *F21Y 2115/10* (2016.08)

(58) Field of Classification Search
CPC .... F21S 8/086; F21S 4/28; F21S 2/005; F21S 8/043; F21S 8/085; F21V 29/76; F21V 21/30; F21V 23/008; F21V 29/74; F21V 21/002; F21V 21/14; F21V 23/003; F21V 23/0435; F21V 21/005; F21V 23/06; H01R 24/84; F21Y 2105/16; F21Y 2115/10
See application file for complete search history.

(56) References Cited

U.S. PATENT DOCUMENTS

| | | | |
|---|---|---|---|
| 9,781,780 B1* | 10/2017 | Van Arendonk | H05B 45/00 |
| 10,356,886 B1* | 7/2019 | Cooley | F21S 10/00 |
| 10,378,742 B1* | 8/2019 | Rao | F21S 9/00 |
| 2008/0094838 A1* | 4/2008 | Russello | F21V 23/0442 362/249.07 |
| 2014/0334149 A1* | 11/2014 | Nolan | F21V 23/005 362/235 |

* cited by examiner

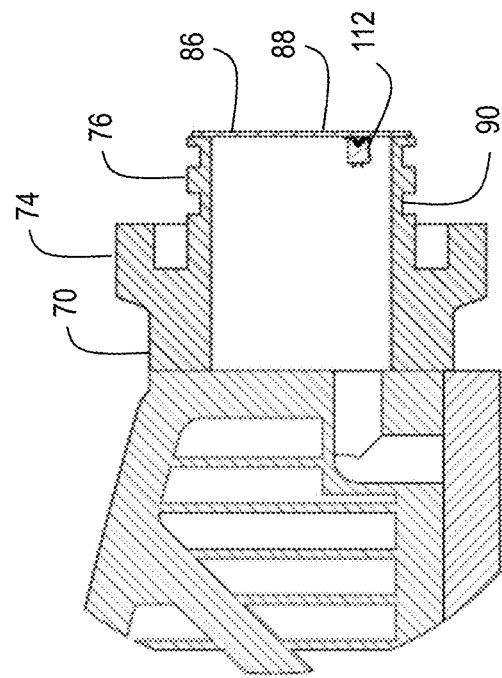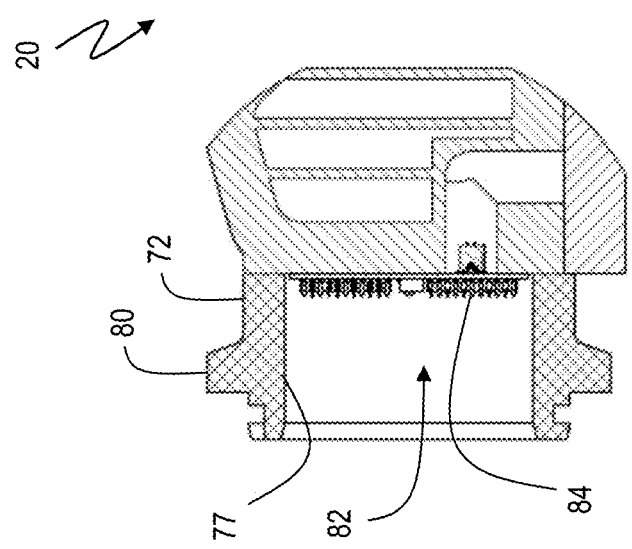
FIG. 8

LIGHTING MODULE WITH CUTOFF TUNING EFFECTS

CROSS-REFERENCE TO RELATED APPLICATIONS

The present application claims priority to U.S. Provisional Application No. 62/940,644, filed on Nov. 26, 2019, hereby incorporated by reference in its entirety.

BACKGROUND OF THE INVENTION

1. Field of the Invention

The present invention relates to sports lighting systems and, more specifically, to a lighting module having an asymmetric illumination source that can provide cutoff tuning effects.

2. Description of the Related Art

Conventional sports lighting systems rely on individual luminaires that are mounted along the cross-arms of a support pole. Each luminaire contains the requisite power conversion and supply electronics and is individually oriented to direct a generally circular beam of light across the area to be illuminated, such as a sporting field or similar venue. As a result, the lighting system requires significant manual intervention during installation and use. For example, individuals must scale the support pole to access the luminaires, whether for establishing or correcting the orientation of the luminaire, for servicing the components of the luminaire, or for replacing a defective luminaire. As establishing the correct lighting pattern for a sporting field upon installation of a lighting system typically requires significant readjustment and realignment of the luminaires, the amount of manual intervention required by conventional systems can be significant. Moreover, there is often a need to adjust the lighting system after installation. Accordingly, there is a need in the art for lighting system that can be more easily adjusted upon installation and during use.

BRIEF SUMMARY OF THE INVENTION

The present invention is an asymmetrically controllable lighting system that allows for adjustment of the illumination produced by the individual luminaires of the system without having to physically reorient the luminaires. More specifically, the luminaires comprise a housing extending along a longitudinal axis and having an elongated opening and an illumination source positioned in the elongated opening of the housing. The illumination source has a plurality of rows of light emitting diodes, each of which is coupled to one of a corresponding plurality of independent electrical power pathways. The plurality of light emitting diodes may extend longitudinally in parallel to the longitudinal axis. The housing includes a coupler positioned at one end of the housing having a plurality of electrical contacts interconnected to plurality of rows of light emitting diodes via each of the independent power pathways. The lighting system of the present invention further comprises an enclosure positioned remotely from the housing and including a plurality of light emitting diode drivers interconnected to the plurality of rows of light emitting diodes by a wiring harness coupled to the plurality of electrical contacts. Each of the plurality of light emitting diode drivers is configured to control the amount of illumination output by a corresponding one of plurality of rows of light emitting diodes using one of the plurality of independent electrical power pathways. Each of the plurality of light emitting diode drivers may also include a local microprocessor responsive to an external command to set the amount of illumination output by the corresponding independently controllable row of light emitting diodes. The lighting system may further include a central microprocessor having a communication interface programmed to be in wireless communication with a remote host. The central microprocessor may be programmed to receive a wireless instruction from the remote host regarding the amount of illumination to be output by one of the plurality of rows of light emitting diodes and to send a corresponding digital command to cause the local microprocessor of the corresponding light emitting diode driver for the one of the plurality of rows of light emitting diodes to cause that light emitting diode driver to set the amount of illumination output by the one of the rows of light emitting diodes.

The present invention also includes a method of adjusting the illumination provided by a lighting system that avoids the physically reorient the luminaires of the system. The first step of the method comprises providing a luminaire having a housing extending along a longitudinal axis and an illumination source positioned in an elongated opening of the housing and having a plurality of rows of light emitting diodes, wherein each of the plurality of rows of light emitting diodes is coupled to one of a corresponding plurality of independent electrical power pathways. The next step of the method comprises independently driving the plurality of rows of light emitting diodes using the plurality of independent electrical power pathways. The plurality of light emitting diodes of each luminaire extend longitudinally in parallel to the longitudinal axis of the housing. The step of independently driving the plurality of rows of light emitting diodes comprises driving the plurality of rows of light emitting diodes so that at least two of the plurality of rows of light emitting diodes are emitting a different amount of illumination. The step of independently driving the plurality of rows of light emitting diodes may also comprise the step of sending a wireless signal to a microprocessor indicating the amount of illumination to be emitted by one of the plurality of rows of light emitting diodes. The step of independently driving the plurality of rows of light emitting diodes may further comprise the step of the microprocessor providing a digital command to a light emitting diode driver associated with the one of the plurality of rows of light emitting diodes to cause the light emitting diode driver to drive the wherein the step of independently driving the plurality of rows of light emitting diodes to produce the amount of illumination indicated by the wireless signal.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 8 is a cross-sectional view of the male and female couplers of a lighting module according to the present invention;

DETAILED DESCRIPTION OF THE INVENTION

Figure 1:
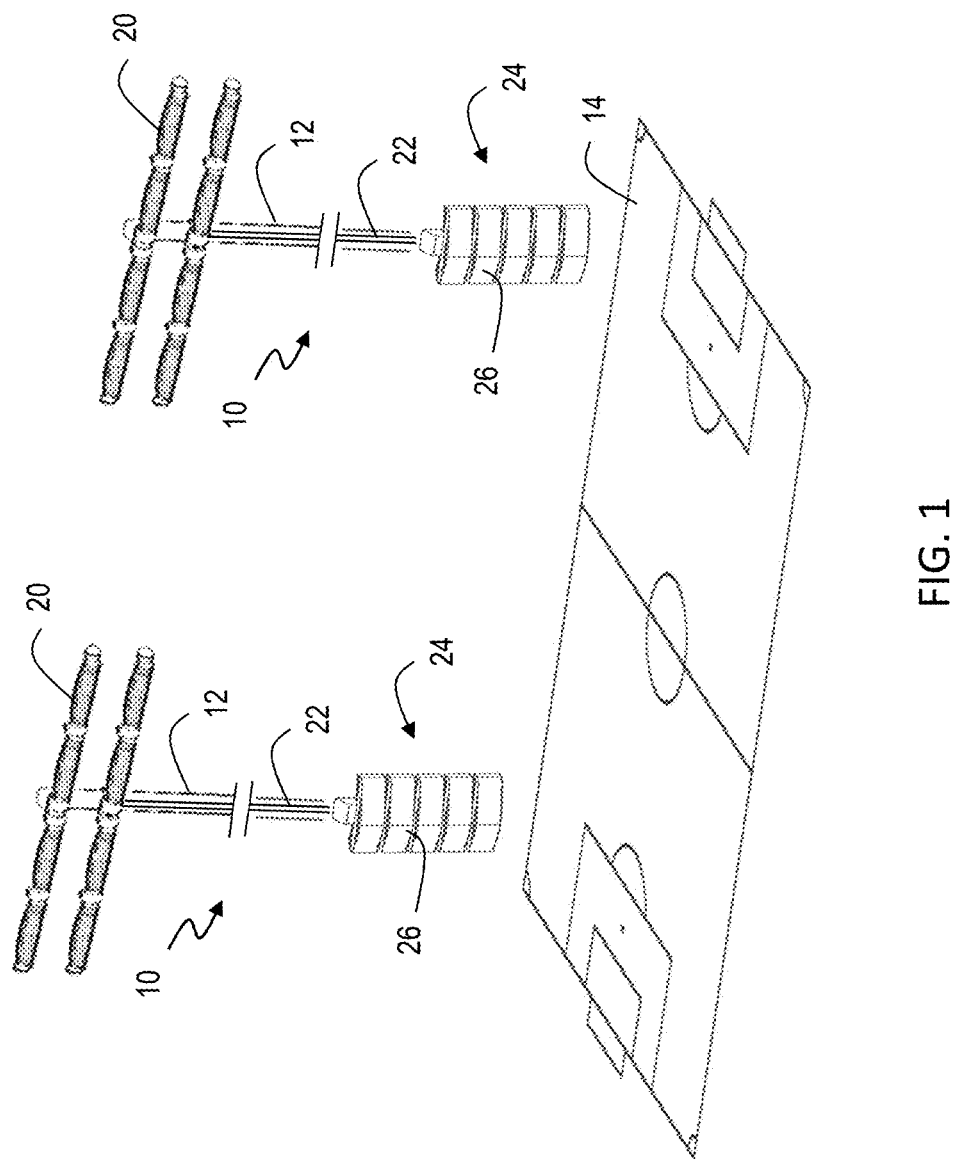
FIG. 1 is a perspective view of an asymmetric source sports lighting system according to the present invention.

Referring to the figures, wherein like numeral refer to like parts throughout, there is seen in FIG. 1 an asymmetric source sports lighting system 10 according to the present invention. System 10 is designed for installation on a support pole 12 to provide illumination over a target area 14, such as a sporting field or pitch. System includes one or more rows of light emitting diode (LED) lighting modules 20 that extend laterally from support pole 12. Lighting modules 20 are powered via a wiring harness 22 that extends along the interior of support pole 12 and is coupled to a controller stack 24. Controller stack 24 transforms local building power from AC to DC and includes LED drivers 26 for lighting modules 20.

Figure 2:
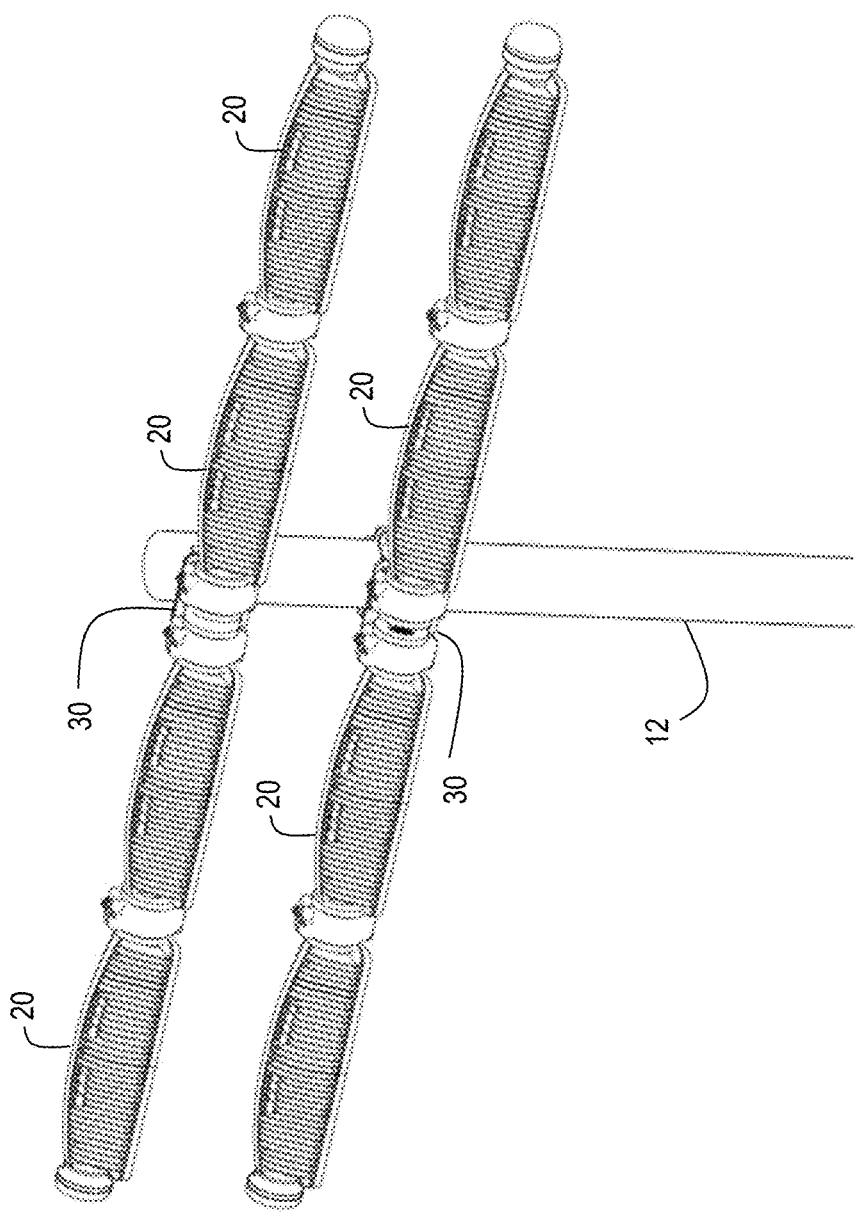
FIG. 2 is a perspective view of the upper portion of a support pole of an asymmetric source sports lighting system according to the present invention.

Referring to FIG. 2, a central mount 30 is coupled to pole 12 and used to support first and second lighting modules 20. Lighting modules 20 are coupled to either side of mount 30 using a modular coupling system described herein that physically supports modules 20 and electronically interconnects modules 20 to wiring harness 22 and thus controller stack 24. The opposing end of each lighting module 20 coupled to mount 30 may be used to physically support and electronically interconnect to additional lighting modules 20 extending further outwardly from support pole 12. The combination of lighting modules 20 connected to mount 30 and the additional lighting modules 20 extending to either side of pole 12 are self-supporting so that support pole 12 does not need to include physical cross-arms or lateral supports to mount additional lighting modules 20. The particular dimensions of lighting module 20 may be varied as desired. For example, lighting module 20 could be provided in two lengths, X and 2X, that may be mixed and matches as needed for a particular installation.

Figure 3:
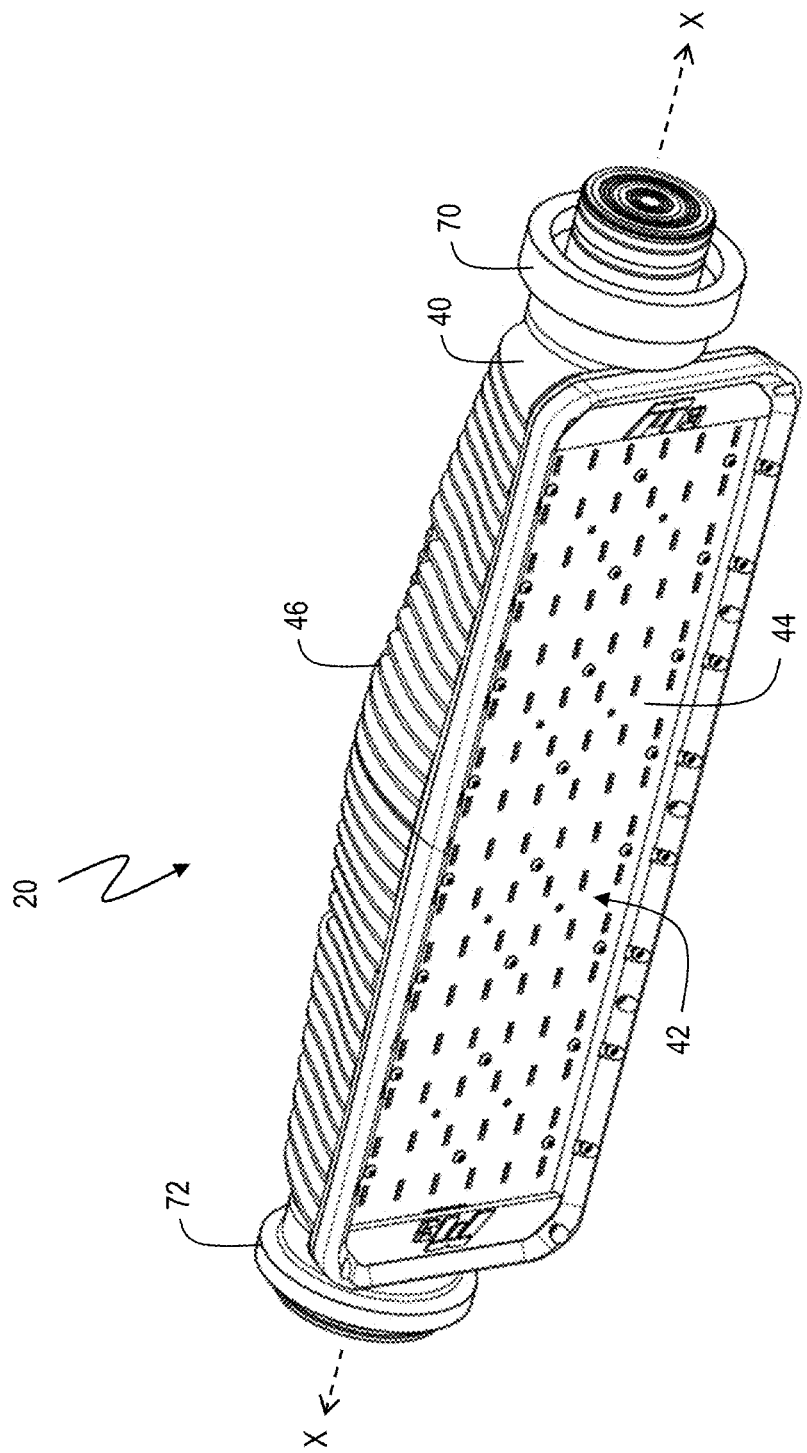
FIG. 3 is a perspective view of the asymmetric lighting source for a lighting module according to the present invention.

Referring to FIG. 3, each lighting module 20 includes a housing 40 extending along a longitudinal axis X-X. Housing 40 defines a rectangular opening 42 in a central portion thereof that permits access to an asymmetric illumination source 44. Asymmetric illumination source 44 is dimensioned to produce an asymmetric beam of illumination from rectangular opening 42 of module 20. Housing 40 may further include fins 46 or other external structures for dispersing heat generated by the use of asymmetric illumination source 44.

Figure 4:
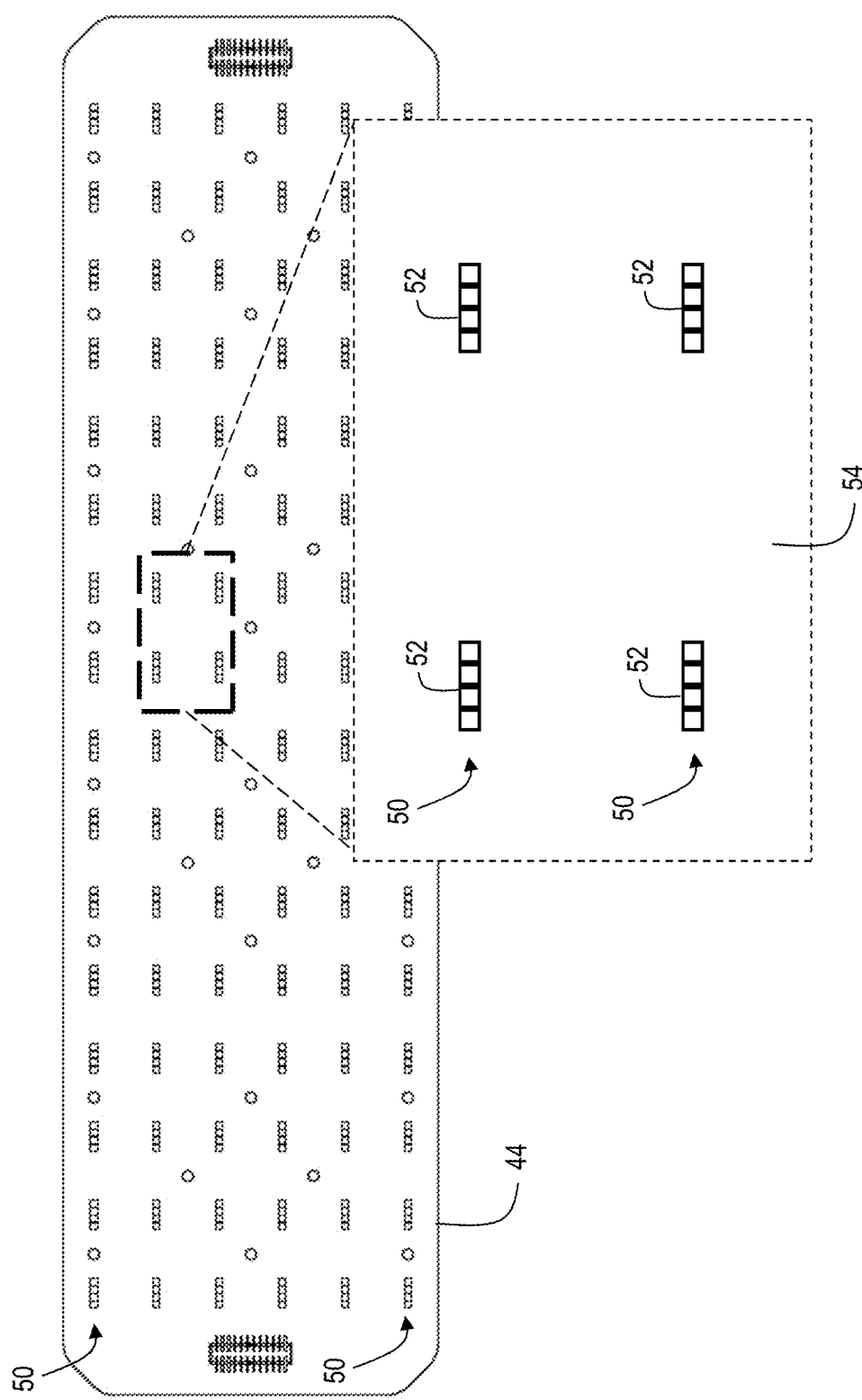
FIG. 4 is a mechanical view of the light emitting diode (LED) layout for an asymmetric lighting source according to the present invention.
Figure 5:
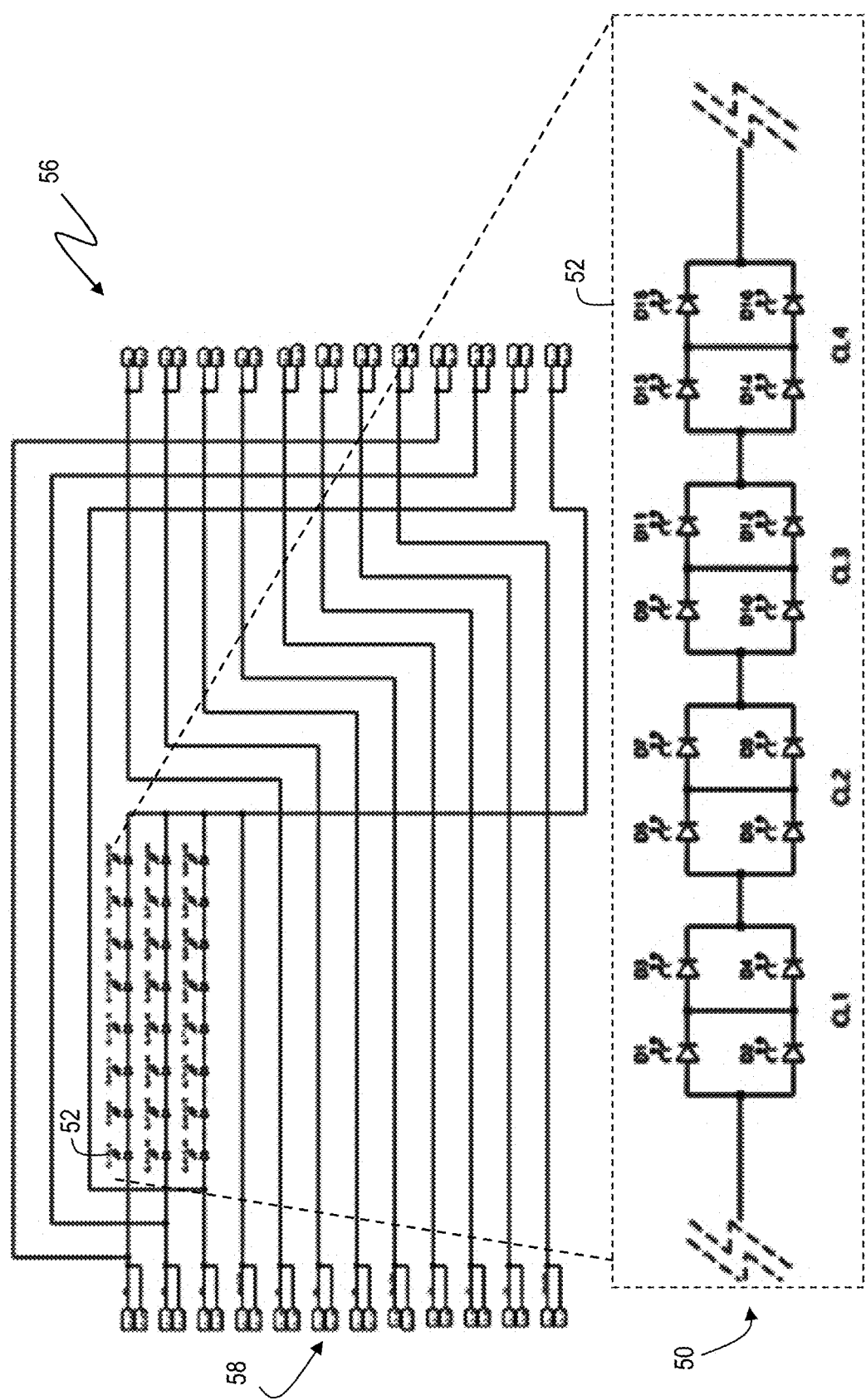
FIG. 5 is schematic of the electronics for an asymmetric lighting source according to the present invention.

Referring to FIGS. 4 and 5, asymmetric illumination source 44 comprises multiple rows 50 of light emitting diode (LED) sets 52 spaced along a substrate 54 and coupled to electronic circuitry 56 for asymmetrically driving illumination source 44. Each row 50, or optionally, each pair of rows 50, are independently controllable by adjusting the amount of power delivered to that row (or pair or rows) using electronic circuitry 56 and controller stack 24 to provide asymmetric illumination from module 20. Optionally, a local microcontroller in each module 20 can be for further adjustment of the amount of power provided to each row (or pair or rows) of LED sets. As seen in FIG. 5, asymmetric illumination source 44 having three independently controllable rows 50 of LED sets 52. Electronic circuitry 56 further includes pass-through circuitry 58 for providing power to adjacently connected lighting modules 20 that also include independently controlled rows 50 of LED sets 52. In the example of FIG. 5, a total of two additional lighting modules 20 may be interconnected and supported by circuitry 58.

Figure 6:
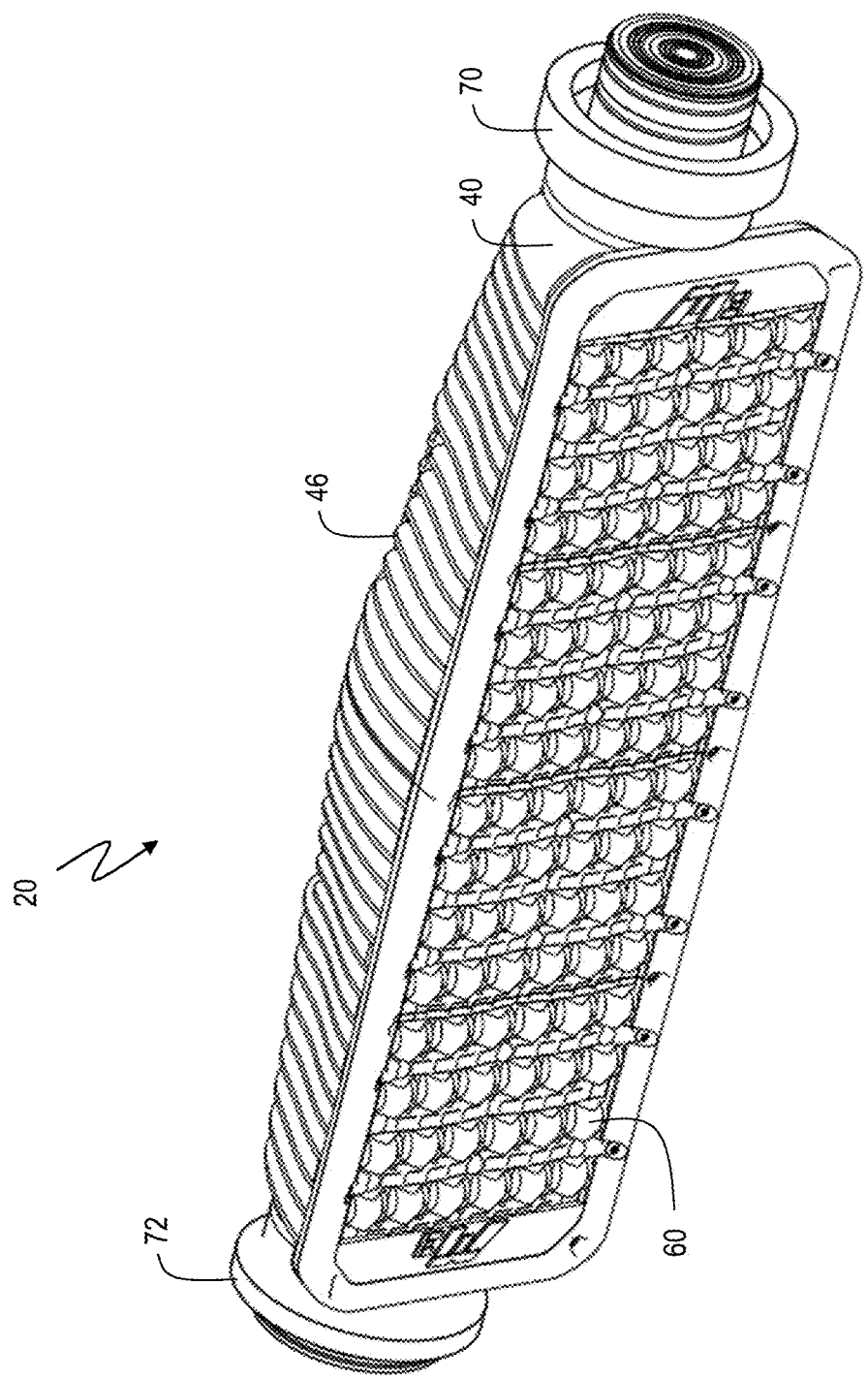
FIG. 6 is a perspective view of a lighting module according to the present invention having a lens array thereon.

Referring to FIG. 6, a molded lens array 60 is positioned over an asymmetric illumination source 44 to reduce harshness and provide sealing of asymmetric illumination source 44 within housing 40. Housing 40 of module 20 is further configured to allow for easy coupling to the support pole and to other housings 40, forming both structural and electrical connection. Housing 40 includes a male coupler 70 positioned at one end of housing 40 and a female coupler 72 positioned at an opposing end of housing 40. Male coupler 70 is defined by a a radially extending flange 74 and a circumferentially extending, outwardly facing bearing surface 76. Female coupler 72 includes a correspondingly dimensioned flange 78 and a receptacle 82 defining a circumferentially extending, inwardly facing bearing surface 77.

Figure 7:
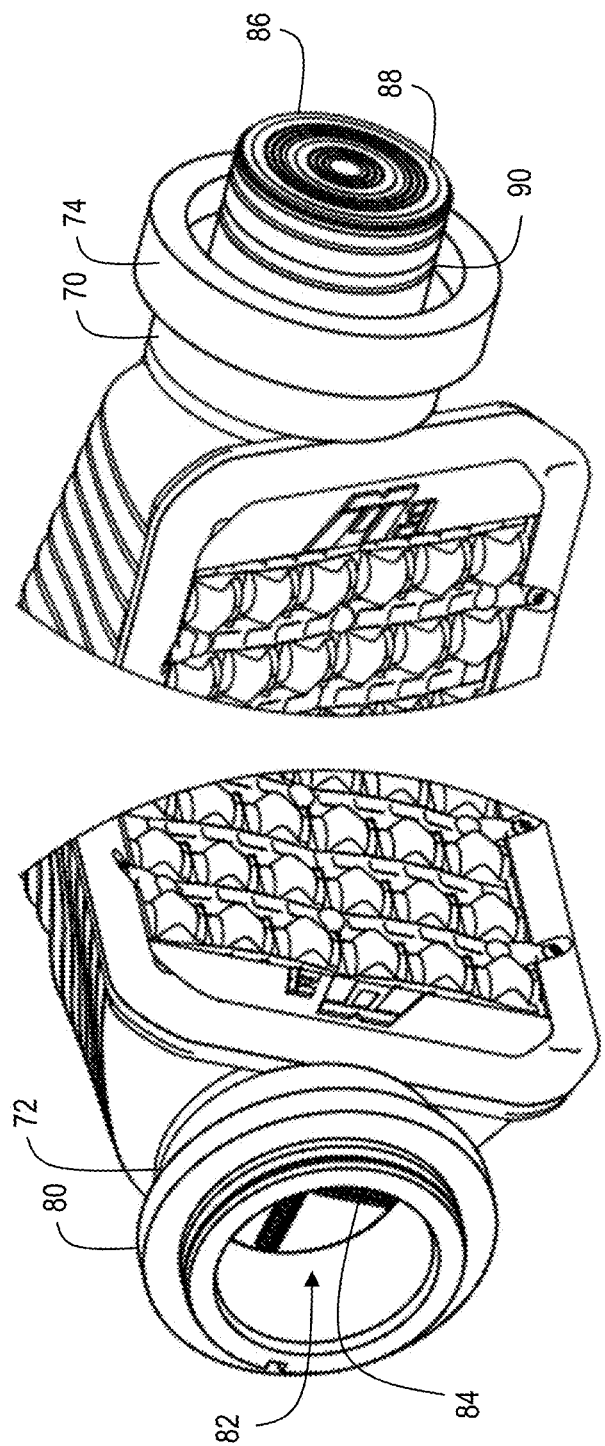
FIG. 7 is a perspective view of the male and female couplers of a lighting module according to the present invention.

Referring to FIGS. 7 and 8, female coupler 72 further includes a set of brush contacts 84 positioned in receptacle 82 that face outwardly along axis X-X and male coupler 70 includes an end face 86 supporting set of ring contacts 88 that face outwardly in the opposite direction along axis X-X from brush contacts 84. Male coupler 70 may additionally include grooves 90 formed therein to house an O-ring for sealing purposes. It should be recognized that other contacts may be used, such as pogo pins and the like. As detailed below, brush contacts 84 and ring contacts 88 define a plurality of independent pathways for powering the independently controlled rows 50 of LED sets 52.

Figure 9:
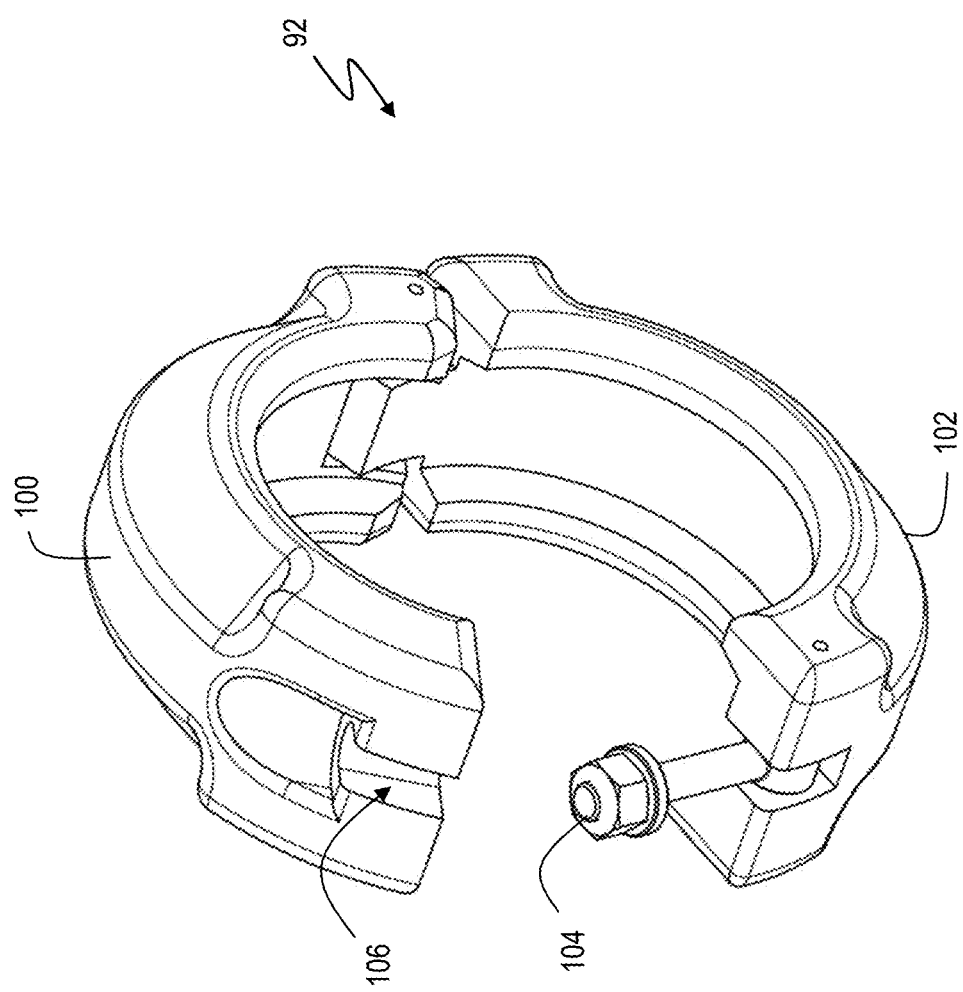
FIG. 9 is a perspective view of a coupler clamp for securing lighting modules to each other according to the present invention
Figure 10:
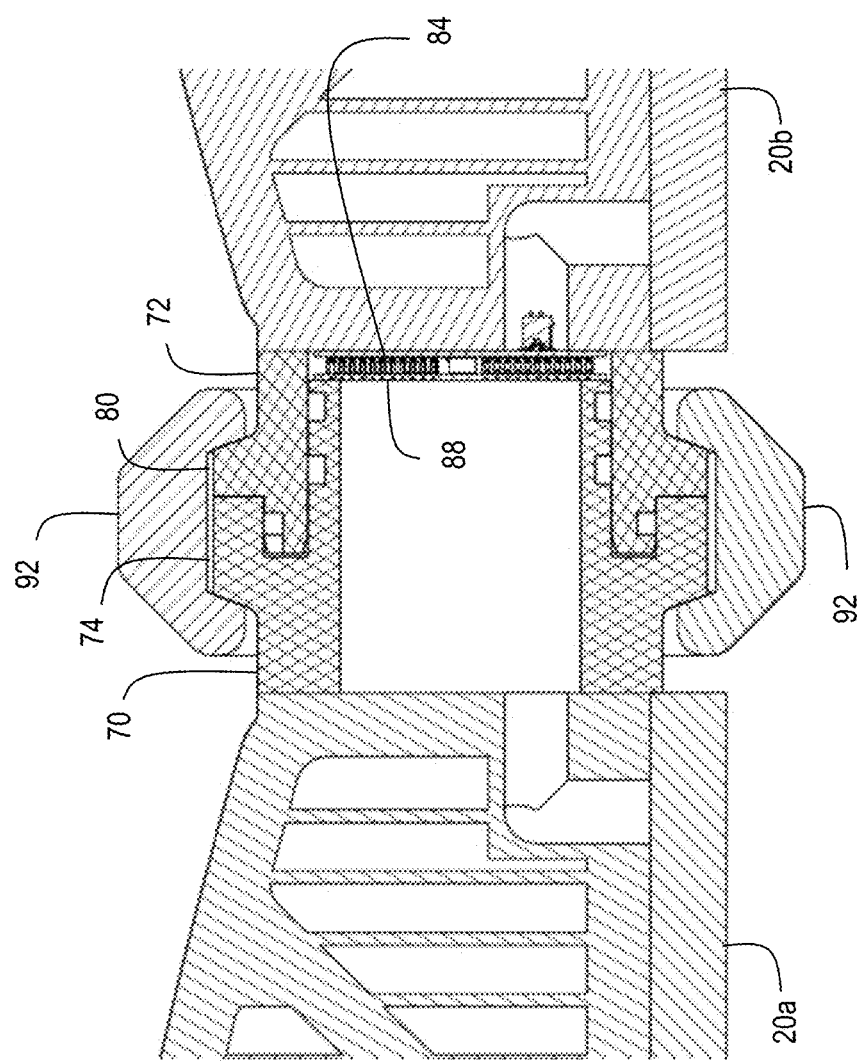
FIG. 10 is cross-sectional view of a lighting module to lighting module connection according to the present invention.

Referring to FIGS. 9 and 10, a clamp 92 may be positioned and secured in covering relation to flanges 74 and 80 to secure a first module 20a to a second module 20b when male coupler 70 and female coupler 72 are full joined so that bearing surfaces 76 and 77 are in seated together and brush contacts 84 and ring contacts 88 are in contact and electrically engaged. Clamp 92 comprises a pair of jaws 100 and 102 that can be opened and then closed in covering relation to flanges 74 and 80, as seen in FIG. 10, when male coupler 70 of one module 20a is jointed with and seated inside female coupler 72 of an adjacent module 20b. When male coupler 70 is fully inserted into female coupler 72, flanges 74 and 80 will abut and brush contacts 84 will physically and electrically engage ring contacts 88. Clamp 92 may then be closed over flanges 74 and 80 to secure first module 20a to second module 20b using a latch 104 on one jaw 102 that cooperates with a slot 106 in the other jaw 100, with electrical continuity between first module 20a to second module 20b provided via the engagement of ring contacts 88 with brush contacts 84. Adjacent modules 20 may thus be electrically interconnected when coupled together so that each module 20 has multiple independent electrical power pathways for driving the independently controllable LED rows of asymmetric illumination source 44.

Figure 11:
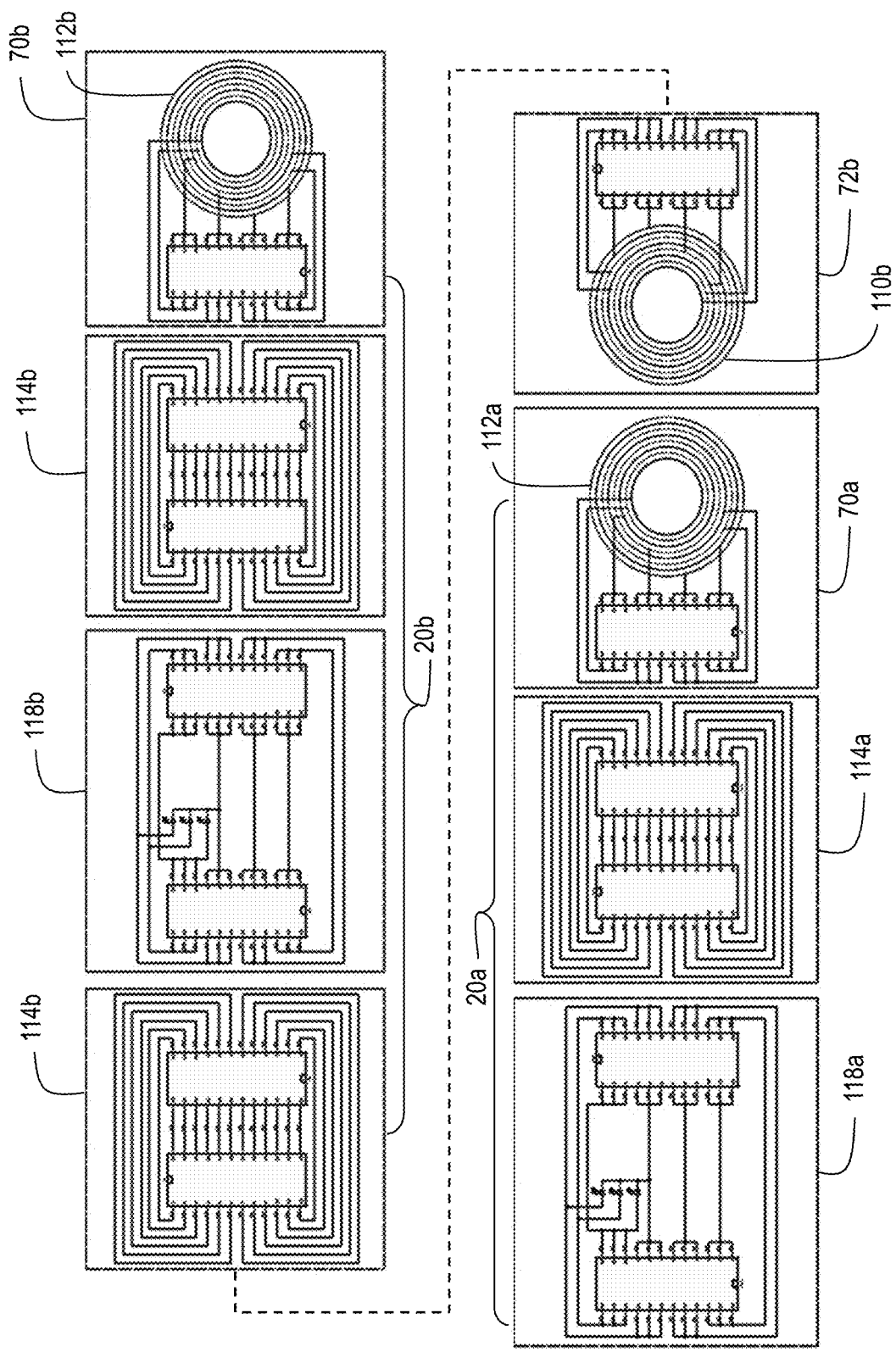
FIG. 11 is an electrical diagram of a lighting module to lighting module connection according to the present invention.

Referring to FIG. 11, module 20b is electrically interconnected to module 20a so that LED circuitry 118b of module 20b and LED circuitry 118a of module 20a are coupled together and under common power control. For example, coupler 70b of module 20b includes coupler circuitry 112b that can receive power from ring contacts 88. Coupler circuitry 112b is coupled to LED circuitry 118b via cabling 114b. LED circuitry 118b is also coupled to coupler circuitry 110b associated with female coupler 72b via cabling 114b. As a result, independent power pathways for LED circuitry 118b extend through module 20b and are available at coupler 70b and coupler 72b such as that a power supply connected to coupler 70 will also provide power to coupler 72, and vice versa. As further seen in FIG. 11, module 20a can be electrically coupled to module 20b via a coupler 70a that is secured to coupler 72b. Coupler circuitry 112a of module 20a is coupled to LED circuitry 114a via cabling 114a. Although not illustrated for simplicity, it should be evident that module 20a also include a coupler 72a that can be, in turn, coupled to another module 20, and so on, with the power supply for all housings 20 connected to an available coupler 70 or 72 at either end. Thus, module 20 is bi-directional and can be placed in series with additional housings 20 for common power control.

Figure 12:
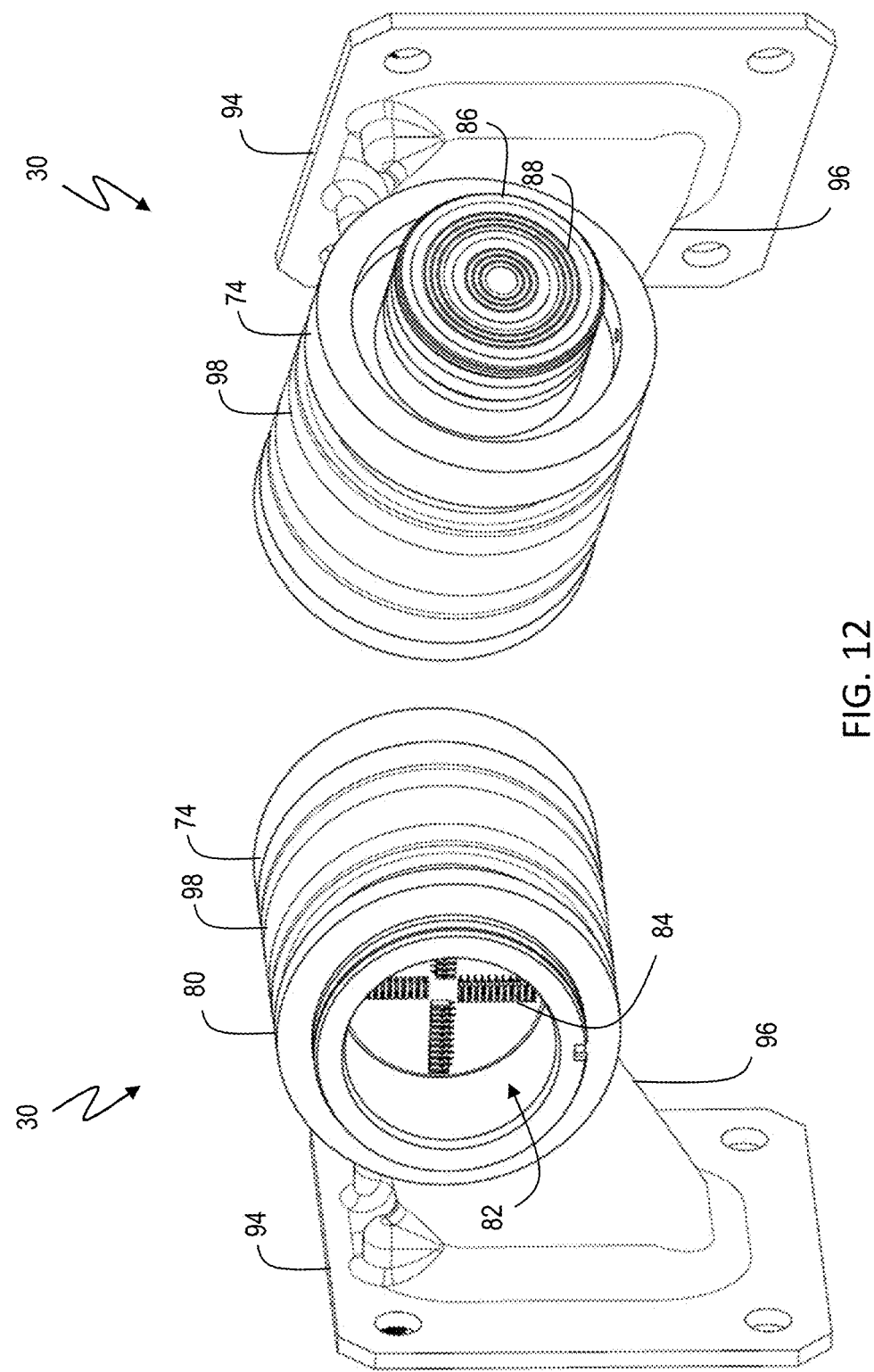
FIG. 12 is two perspective views of a mount according to the present invention.

Referring to FIG. 12, mount 30 for attaching one or more housings 20 to a support pole 12 comprises a mounting plate 94 having a shaft 96 extending therefrom to support a main body 98 having male coupler 70 on one side and a female coupler 72 on the opposing side. Mount 30 suspends module 20 in spaced relation to support pole 12 to which mount 30 is attached. Male coupler 70 and female coupler 72 are configured in same manner as described above with respect to module 20, i.e., male coupler 70 includes an end face 86 having concentric ring contacts 88 and female coupler 72 has brush contacts 84 positioned within receptacle 82. Male coupler further includes flange 74 and female coupler 72 includes flange 80. As a result, module 20 may be coupled to mount 30 in the same manner as described above with respect to the connection of module 20a to module 20b.

Figure 13:
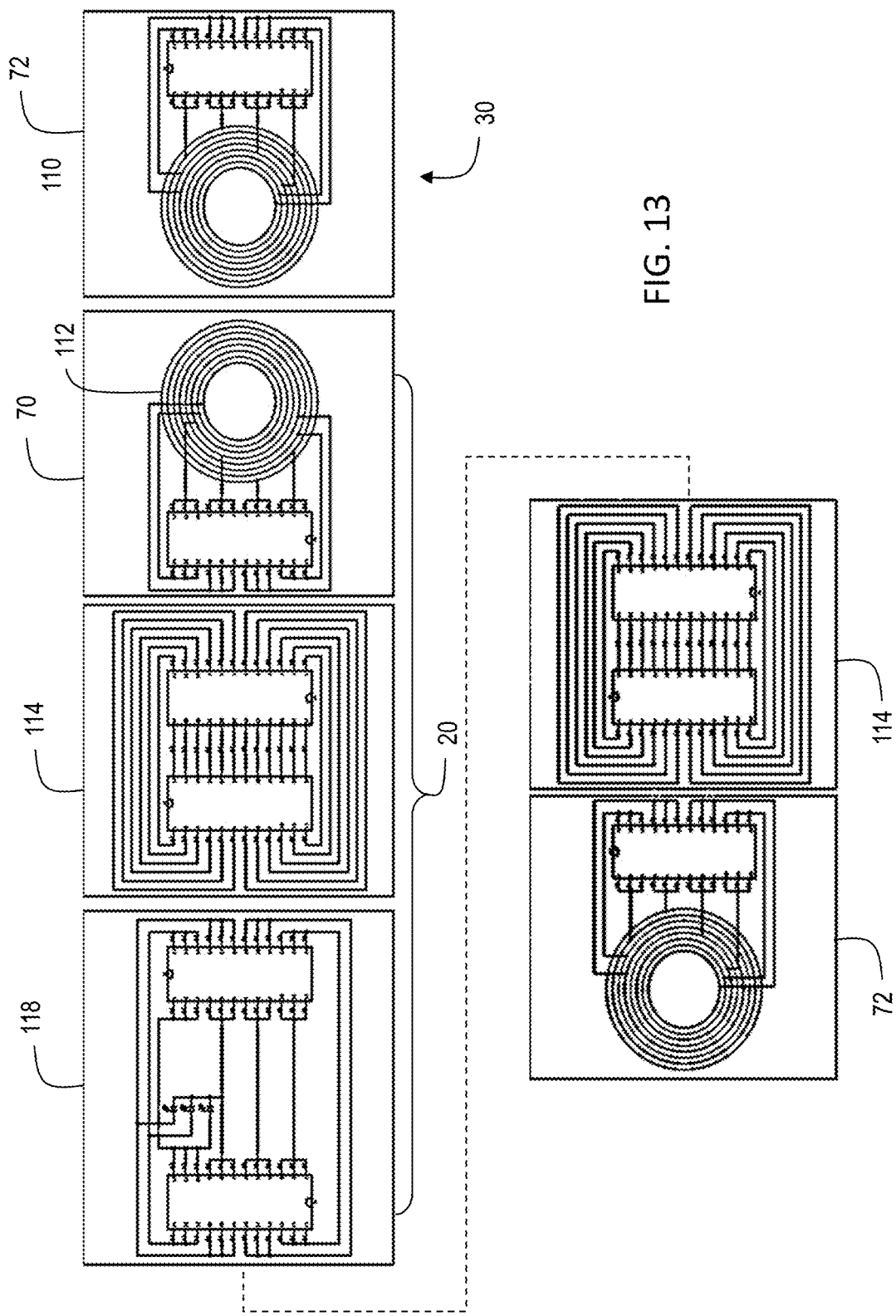
FIG. 13 is an electrical diagram of a lighting module to mount connection according to the present invention.

Referring to FIG. 13, joining of mount 30 to module 20 allows coupler circuitry 110 of female coupler 72 of mount 30 to connect with coupler circuitry 112 of male coupler 70 of module 20 via brush contacts 84 and ring contacts 88. Coupler circuitry 112 is coupled to LED circuitry 118 via cabling 114. LED circuitry 118 is also coupled to coupler circuitry 110 associated with female coupler 72 via cabling 114. As a result, independent power pathways for LED circuitry 118b extend through module 20 from mount 30 and are available at coupler 70 such that a power supply connected to coupler 72 will also provide power to coupler 70. Similarly, module 20 may also be connected to the male coupler 70 of mount 30 using female coupler 72 of module 20, thus simply reversing the connections of FIG. 13 such that power is provided by mount 30 to coupler 72 with the power also made available at coupler 70 for attachment of another module 20.

Figure 14:
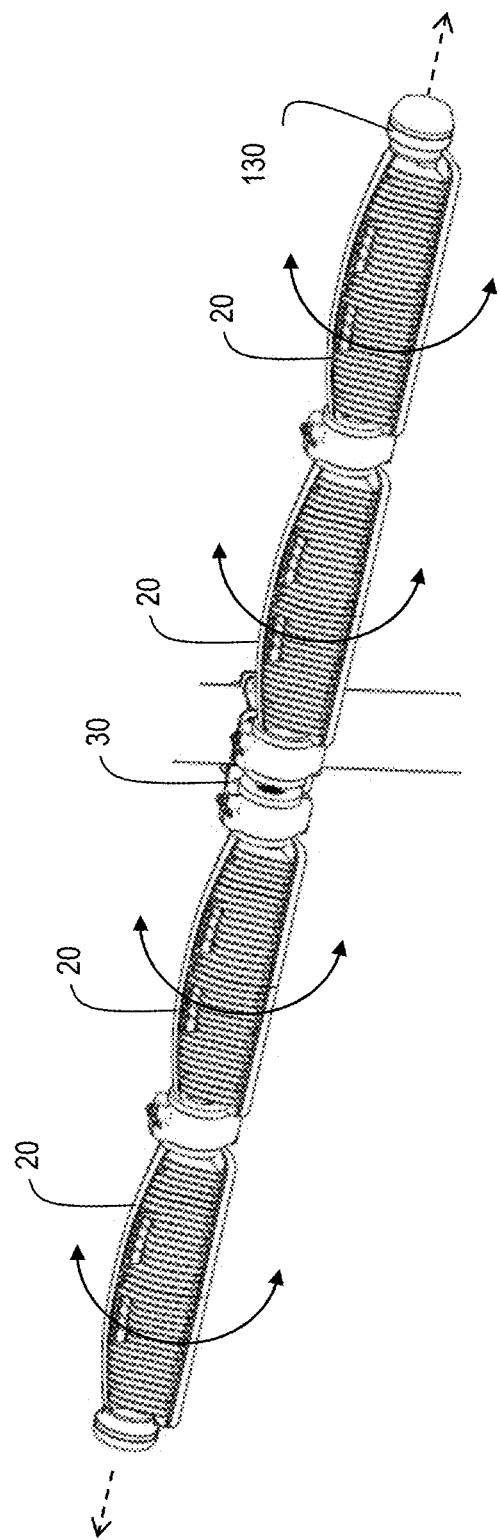
FIG. 14 is a perspective view showing axial rotation of a series of interconnected lighting modules according to the present invention.

Referring to FIG. 14, cylindrical bearing surfaces of male coupler 70 and female coupler 72 allows adjacent lighting modules 20, as well as lighting modules 20 coupled to mount 30, to be rotated about longitudinal axis X-X. The orientation of the rectangular illumination provided by module 20 may thus be adjusted in a single direction, i.e., about a single axis, via rotation of lighting module 20 about axis X-X. As explained above, bearing surfaces 76 and 77 allow for physical rotation of housings 20, with brush contacts 84 and ring contacts 88 maintaining electrical continuity regardless of the rotation of housing about longitudinal axis X-X. Housings 20 may thus be easily oriented, or reoriented, as desired. While housings 20 may be manually adjusted at any time, servo motors could be incorporated into couplers 70 and 72 to allow for remote rotation of lighting modules 20 about axis X-X.

Figure 15:
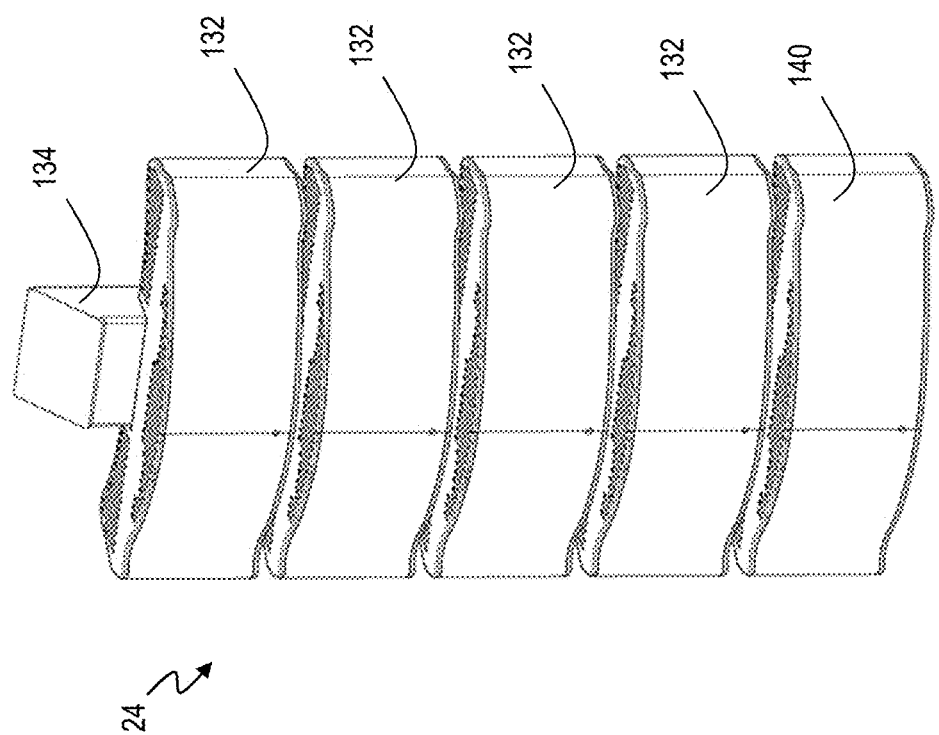
FIG. 15 is a perspective view of a controller stack according to the present invention.
Figure 16:
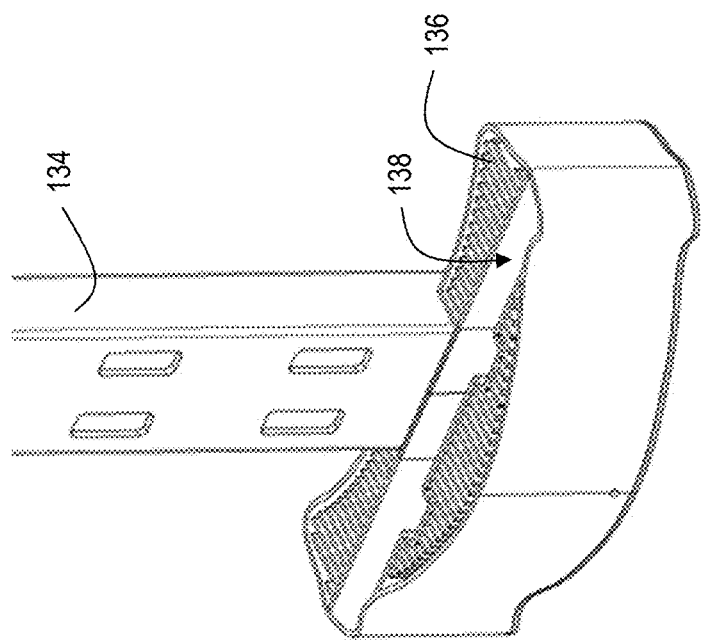
FIG. 16 is a perspective view of a core enclosure according to the present invention.

Referring to FIGS. 15 and 16, controller stack 24 comprises a series of core enclosures 132, each of which houses the power conversion and LED electronics, typically referred to as LED drivers, for an associated lighting module 20, as well as a master enclosure 140 that provides housekeeping functions. Controller stack 24 includes a back plane 134 that provides the electrical interconnections between each core enclosure 132 and master enclosure 140 as well as the requisite interconnections to wiring harness 22 to interconnect controller stack 24 to lighting modules 20. Back plane 134 is preferably adapted to act as a heat sink and transfer excess heat to support pole 12 for additional dispersion of heat generated by controller stack 24. As seen in FIG. 16, core enclosure 132 and/or master enclosure 140 include ribs 136 for dissipation of heat generated by internal electrical components positioned in a central cavity 138.

Figure 17:
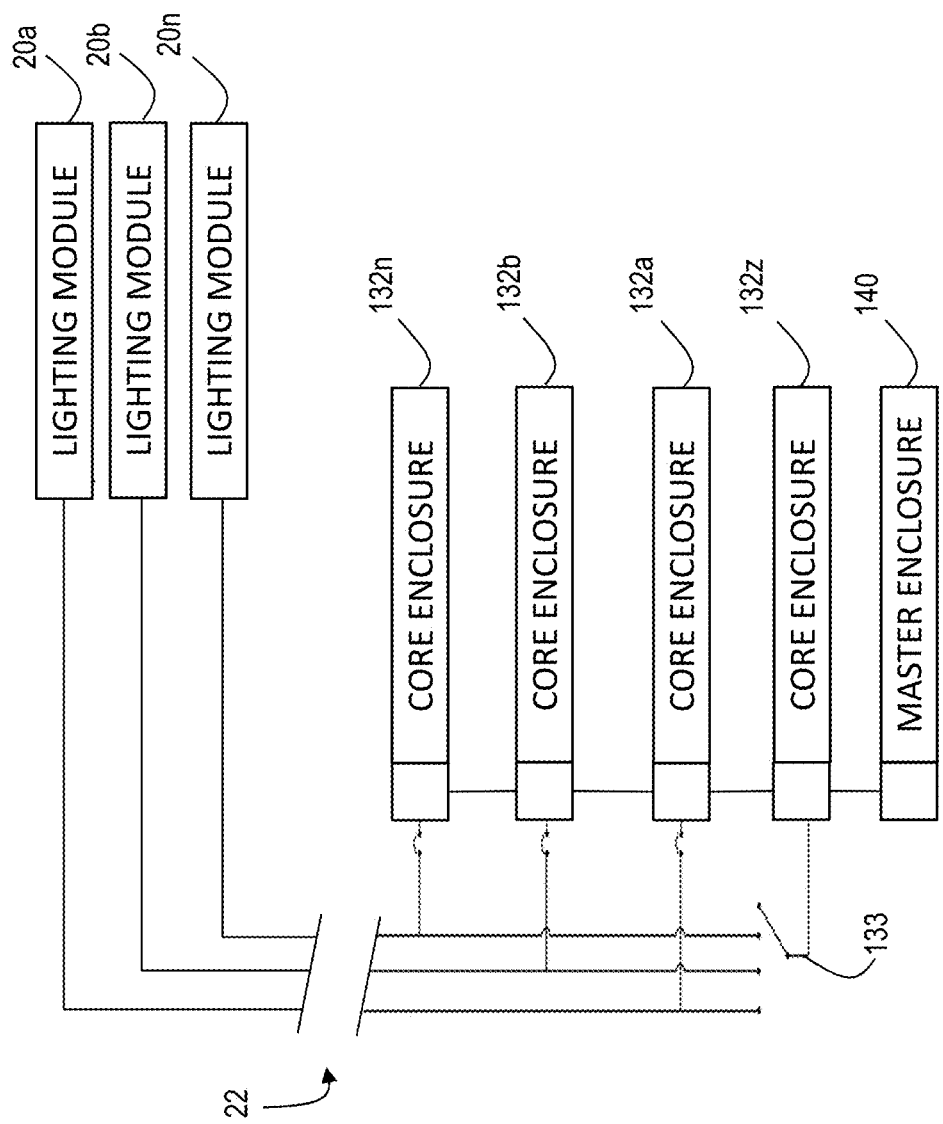
FIG. 17 is high level schematic for a lighting system according to the present invention.

Referring to FIG. 17, each core enclosure 132a, 132b . . . 132n is associated with and coupled via wiring harness 22 to a corresponding lighting module 20a, 20b . . . 20n. Preferable, a backup core enclosure 132z is selectively coupled to each lighting module 20a, 20b . . . 20n via a switching circuit 133 to provide a backup power supply in the event of a fault in any of core enclosure 132a, 132b . . . 132n. For example, if a fault in any core enclosure 132 results in the loss of illumination from any or all of the independently controlled rows 50 of LED sets 52 in the corresponding lighting module 20, power to that lighting module 20 can be switched to the backup core enclosure 132z to maintain the desired amount of illumination until such time as the faulty core enclosure 132 can be repaired or replaced. Each core enclosure 132a, 132b . . . 132n is also interconnected to master enclosure 140, which supervises and controls via digital commands the local operation of each core enclosure 132a, 132b . . . 132n.

Figure 18:
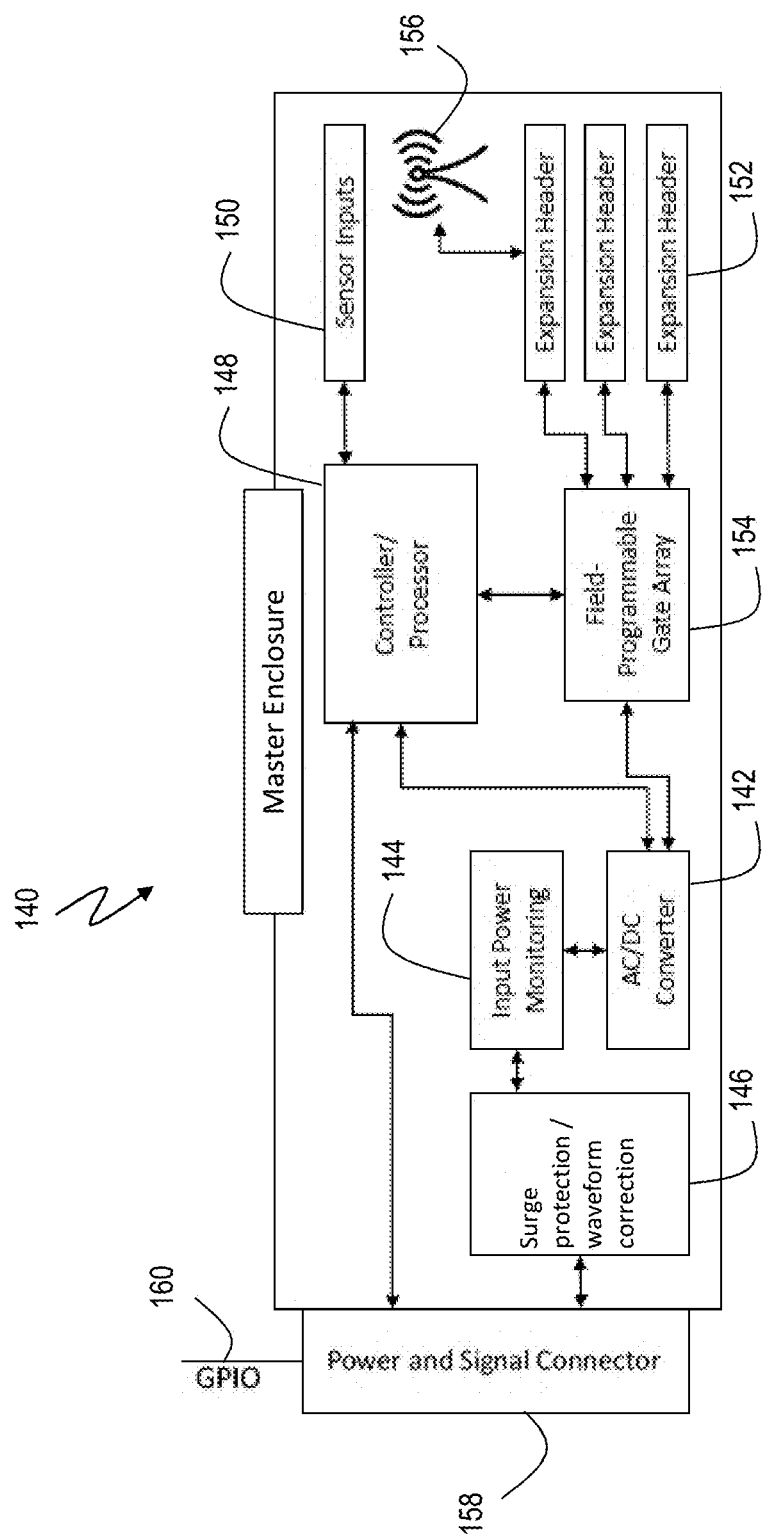
FIG. 18 is a detailed schematic of a master controller according to the present invention.

Referring to FIG. 18, master enclosure 140 is coupled to AC power via a power and signal connector 158 and includes local AC/DC conversion 142 with input power monitoring 144 as well as surge protection and waveform correction 146. Master enclosure 140 also includes a controller/processor 148 that has sensor inputs 150 for monitoring of system 10. Controller/processor 148 is also interconnected to a series of expansion headers 152 and wireless communication interface 156 via a field programmable gate array (FPGA) 154.

Controller/processor 148 may thus be programmed to establish connection with a remotely positioned host system or remote device (such as a tablet or smartphone) that can provide commands controlling operation of lighting modules 20 using expansion headers 152 to provide the desired wireless connectivity. Communication could comprise any conventional wireless communication technology or protocol, such as WiFi, Blutetooth®, BLE, ZigBee, Z-Wave, 6loWPAN, NFC, cellular such as 4G, 5G or LTE, RFID, LoRA, LoRaWAN, Sigfox, NB-IoT, or LIDAR. Controller/processor 148 is also coupled via power and signal connector 158 for communication with core enclosures 132, such as via a general-purpose input/output (GPIO) line 160, extending in back plane 134.

Figure 19:
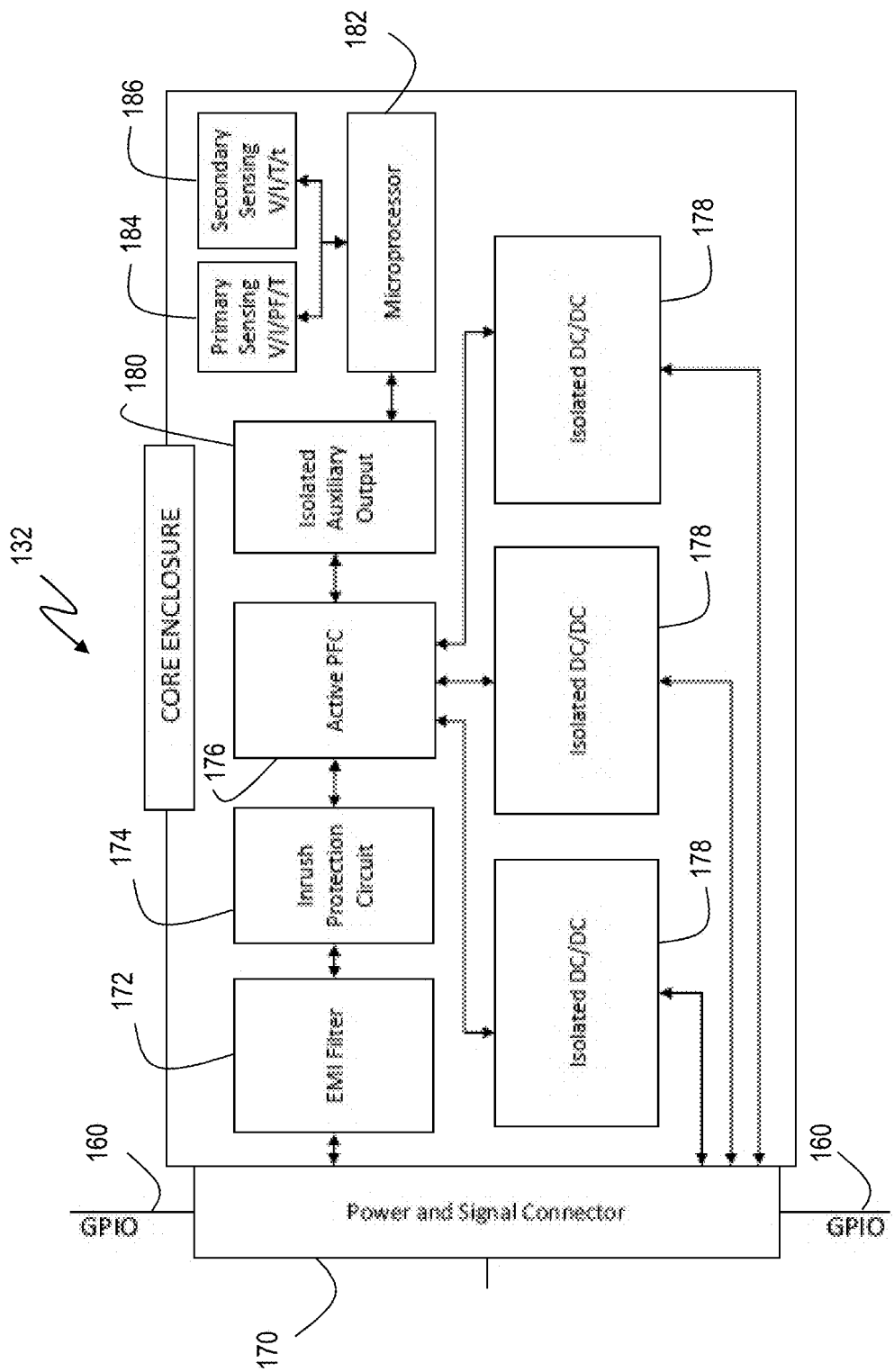
FIG. 19 is a detailed schematic of a core enclosure according to the present invention

Referring to FIG. 19, each core enclosure 132 includes a power and signal connector 170, which provides connectivity to master enclosure 140 via GPIO line 160 as well as to a connection to AC power. Core enclosure 132 provides power conversion to DC and power conditioning via an EMI filter 172, an inrush protection circuit 174 and an active power factor corrector (PFC) 176. A plurality of isolated DC/DC circuits 178, each of which supports a corresponding one of independently controllable LED rows of asymmetric illumination source 44, are coupled to active PFC 176. The present invention is illustrated with three isolated DC/DC circuits because the exemplary illumination source 44 has three independently powered rows of LEDs, but if asymmetric illumination source 44 included four independently controlled rows 50 of LED sets 52, four isolated DC/DC circuits 178 would be included. Core enclosure 132 further comprises an isolated auxiliary output 180 coupled to a microprocessor 182. Microprocessor 182 is further coupled to primary sensing circuits 184 and secondary sensing circuits 186 for monitoring voltage, current, power factor, and temperature across system 10. Microprocessor 182 is further configured to adjust the power output from each of the plurality of isolated DC/DC circuits 178 based on monitoring of primary sensing circuits 184 and secondary sensing circuits 186. For example, if one of independently controlled rows 50 of LED sets 52 is not operational, microprocessor 182 can adjust the power output from the isolated DC/DC circuits 178 for the other of the independently controlled rows 50 of LED sets 52 to compensate for the loss and ensure that asymmetric illumination source 44 is providing the desired amount of illumination.

Figure 20:
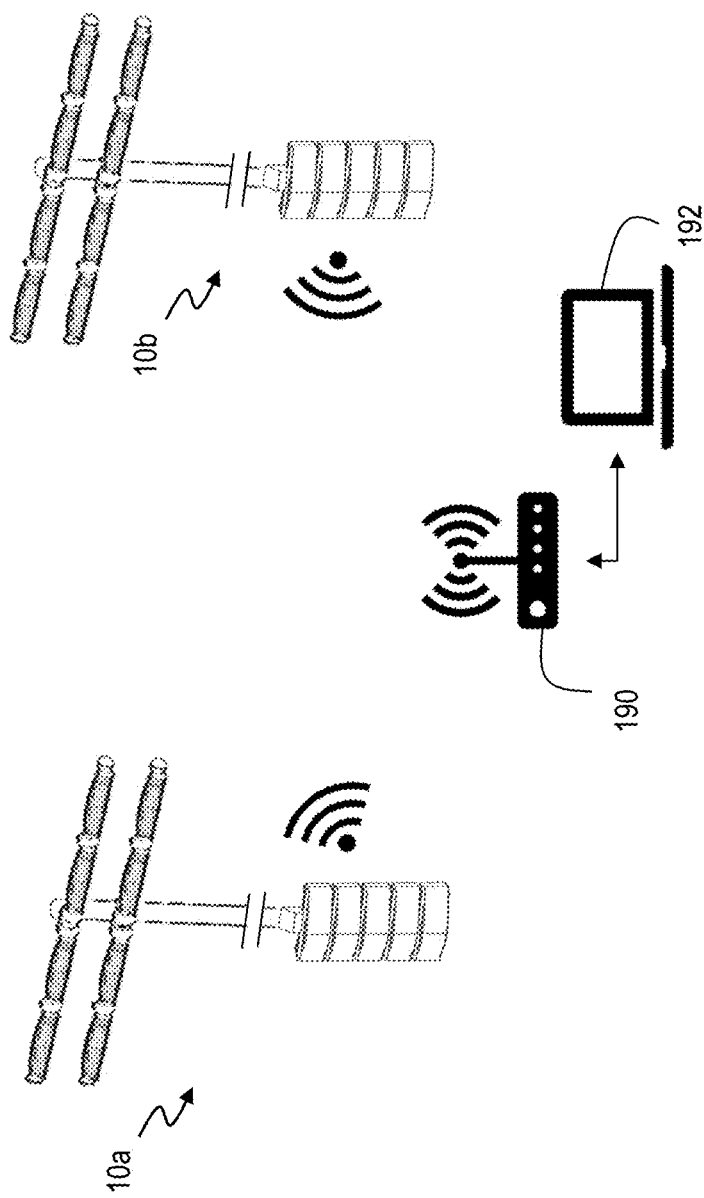
FIG. 20 is a schematic of wireless monitoring and control approach according to the present invention.

Referring to FIG. 20, the wireless communication capability of master enclosure 140 provides a third layer of redundancy in the event of a partial or total loss of illumination from lighting module 20. For example, a detected loss at one location of system 10a may be communicated to wireless gateway 190 and remote host 192. The illumination output of another system 10b may then be adjusted accordingly, either by allowing a user to send a command to system 10b to adjust power to lighting modules 20 to compensate for the detected loss or by supervisory software residing on host 192 that automatically sends the appropriate commands.

Figure 21:
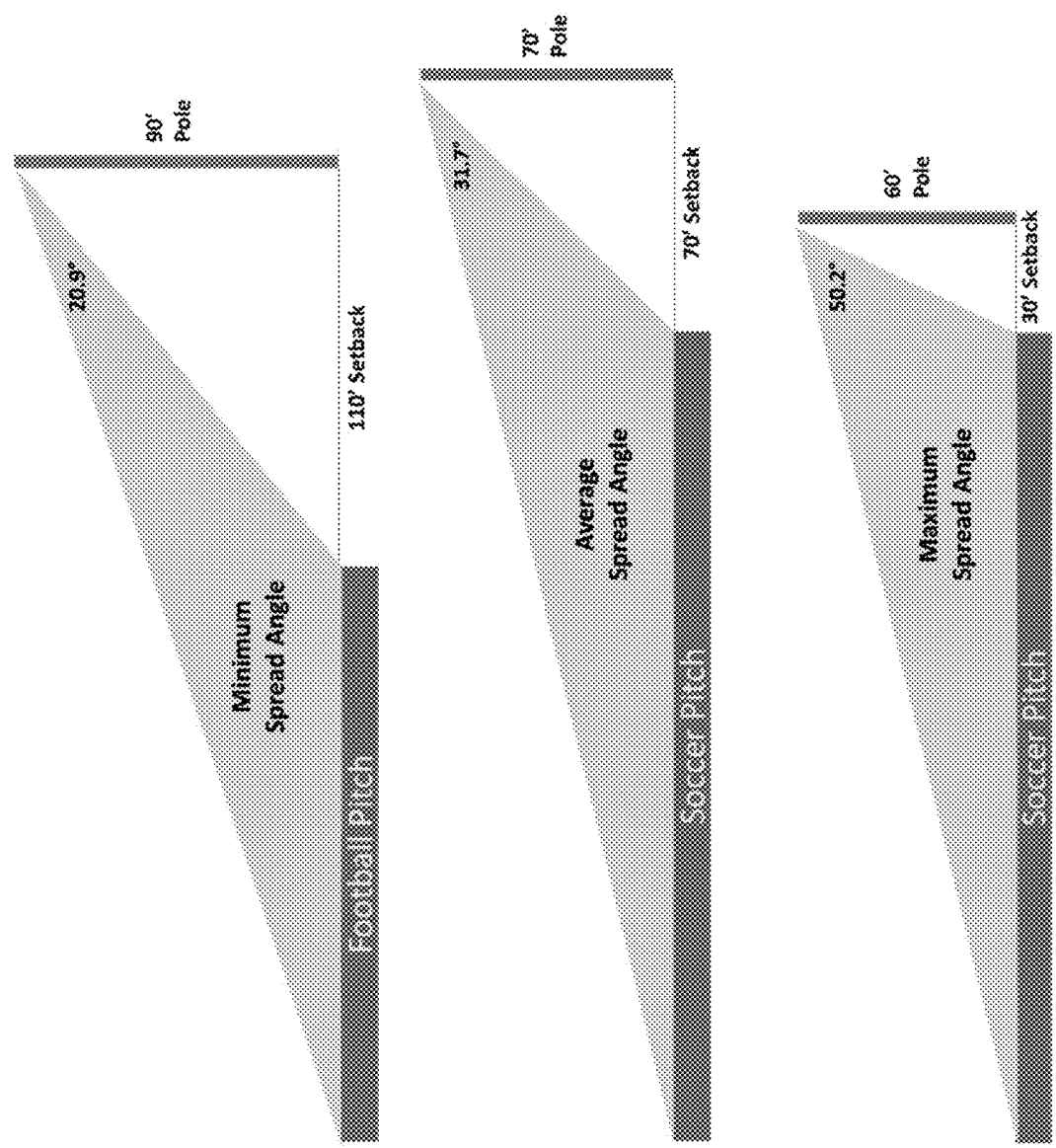
FIG. 21 is a schematic of beam steering using a lighting system according to the present invention.
Figure 22:
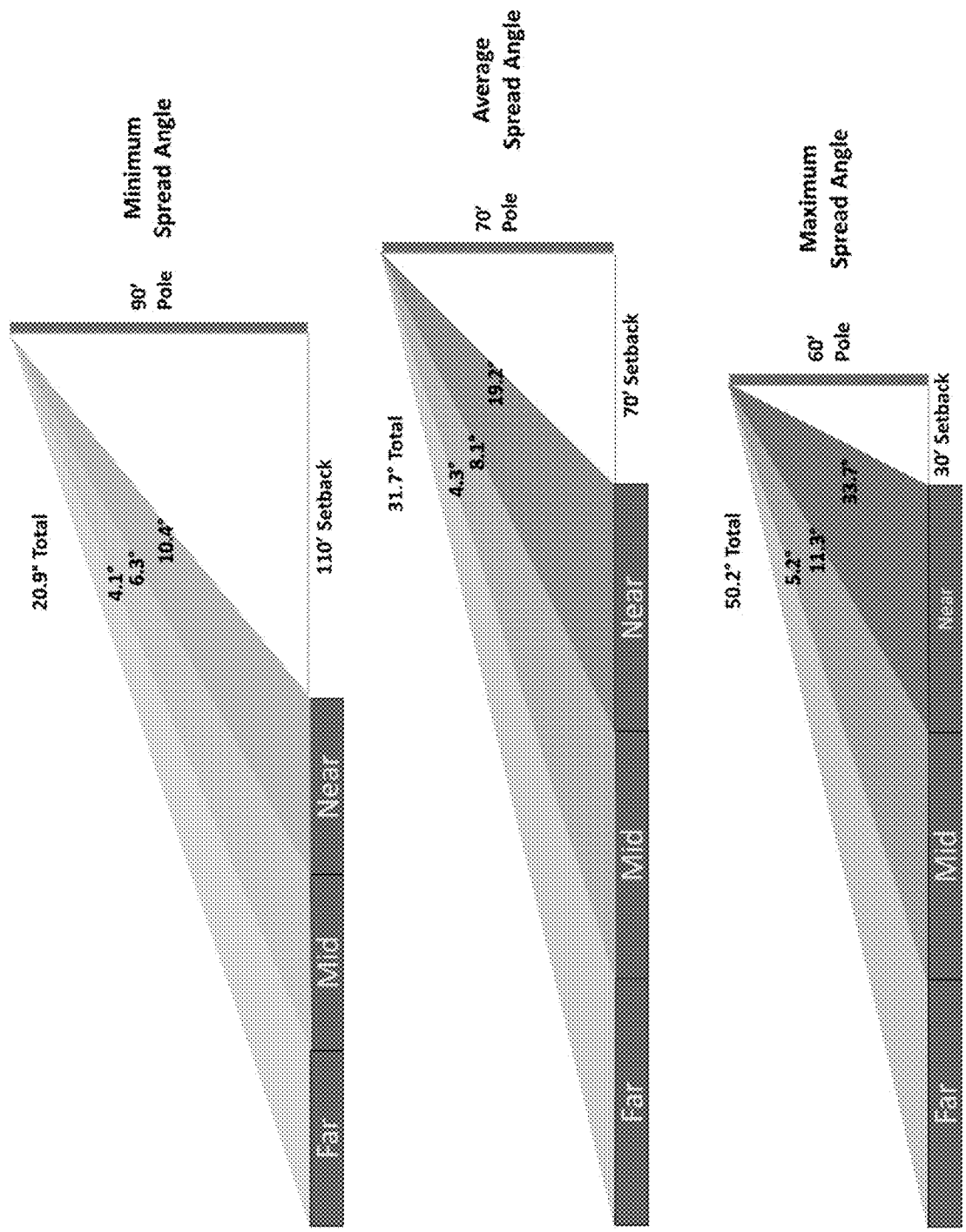
FIG. 22 is a schematic of beam angles changes using a lighting system according to the present invention.

Referring to FIG. 21, asymmetric illumination source 44 of each module 20 allows for remote beam steering of lighting system 10. Lighting system 10 may be adapted to a particular installation regarding of the width of the pitch to be illuminated, the height of support pole 12, and the distance between support pole 12 and the targeted pitch. For example, asymmetric illumination source 44 may be driven to change the beam angle (generally recognized as the region of illumination with at least fifty percent of the maximum beam strength) to provide the appropriate amount of illumination between a minimum and maximum spread angle encountered in an installation. In the first scenario of FIG. 19, where the height of support pole 12 and setback distance require a minimum spread angle, asymmetric illumination source 44 can be driven asymmetrically in a first configuration to provide a narrow beam angle without having to physically reorient modules 20. In the last scenario, where the height of pole 12 and setback distance require a minimum spread angle, asymmetric illumination source 44 can be driven asymmetrically in a different configuration to provide a broader spread angle without having to physically reorient modules 20. Thus, the effective positioning of modules 20 can be adjusted without actually having to physically reorient modules 20. Thus, modules 20 may be asymmetrically driven to change the illumination scenario for different events or conditions, or to simply adjust the illumination in a given location without having to physically move lighting modules 20. FIG. 20 illustrates how the power control over each row 50 of asymmetric illumination source 44 can be adjusted to impact the beam angle emitted from lighting module 20 without having to rotate lighting module 20.

Figure 23:
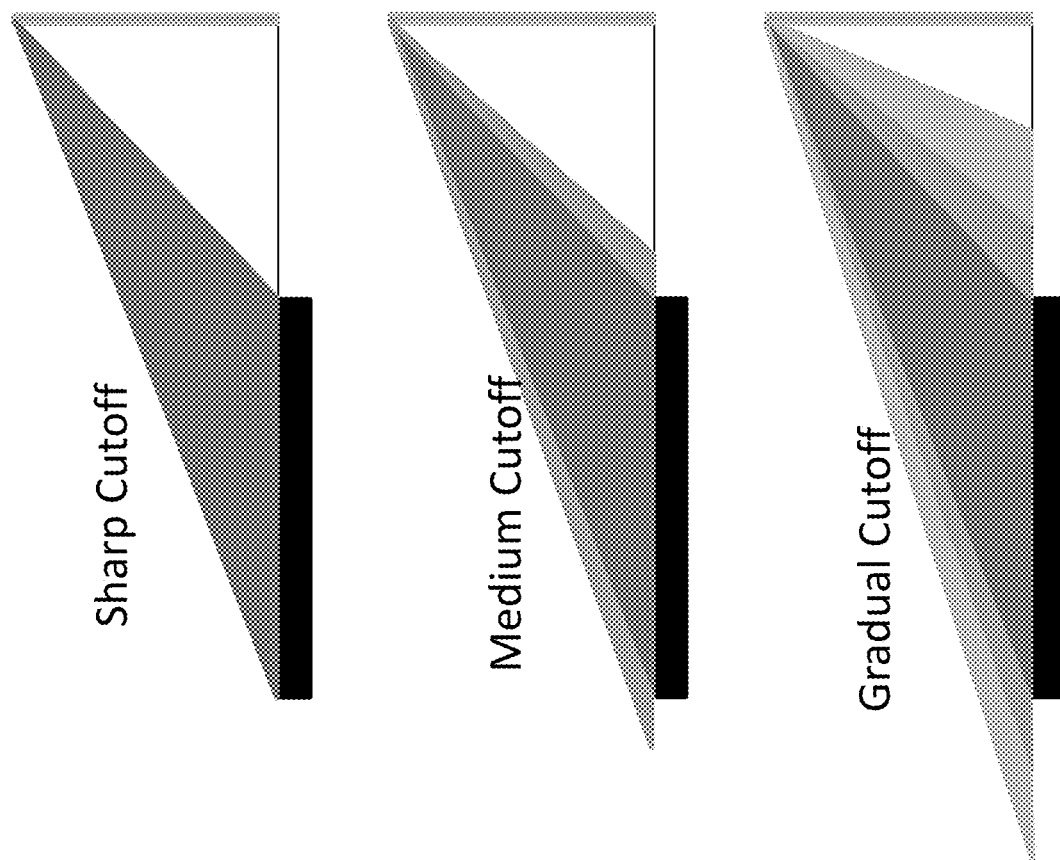
FIG. 23 is a schematic of tunable cut-off in a lighting system according to the present invention.

Referring to FIG. 23, asymmetric illumination source 44 of each lighting module 20 provides for a tunable cut-off for the illumination generated from lighting module 20. Illumination cut-off generally refers to the amount of illumination in the beam field that extends beyond the desired beam angle (any area of illumination with less than fifty percent but more than ten percent of the maximum beam strength). For example, in the first scenario of FIG. 23, the cut-off is very sharp, i.e., there is very little spillage beyond the main beam angle. In the second and third scenarios, the spillage increases such that more illumination is provided ancillary to the primary beam angle. Asymmetric illumination source 44 may be driven to change the cut-off at any time, whether finally upon installation, or dynamically over time to change the lighting scheme as desired by a user for different applications. For example, a gradual cut-off may be selected when more light is desired in the areas surrounding a pitch for a particular event, such as a pre-game show, and then adjusted to provide a sharp cut-off during a game. Thus, asymmetric illumination source 44 allows for control over both the beam angle and the beam field relative to each other and relative to the illumination target.

Figure 24:
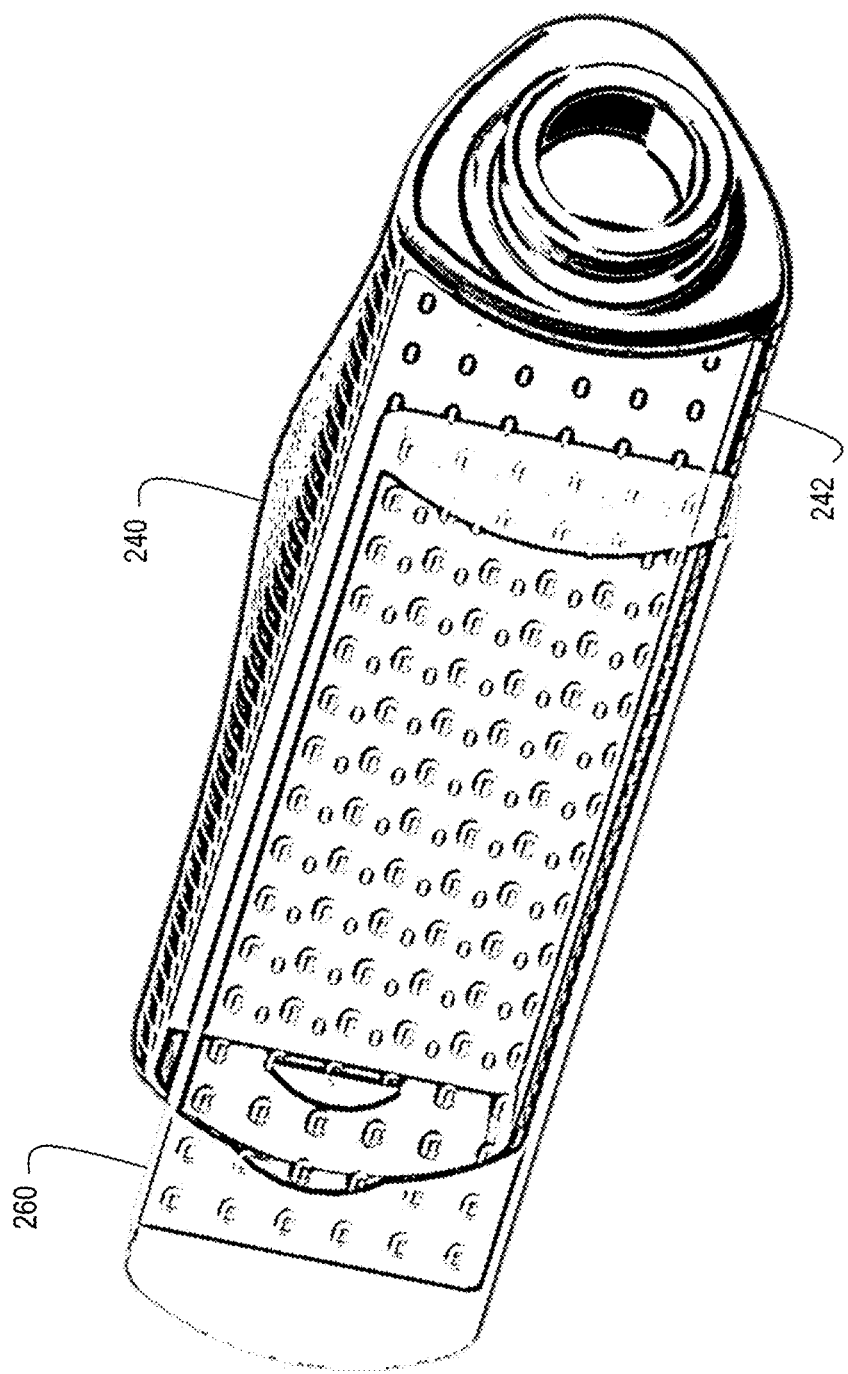
FIG. 24 is a perspective view of an environmental sealing system for a lighting module according to the present invention.
Figure 25:
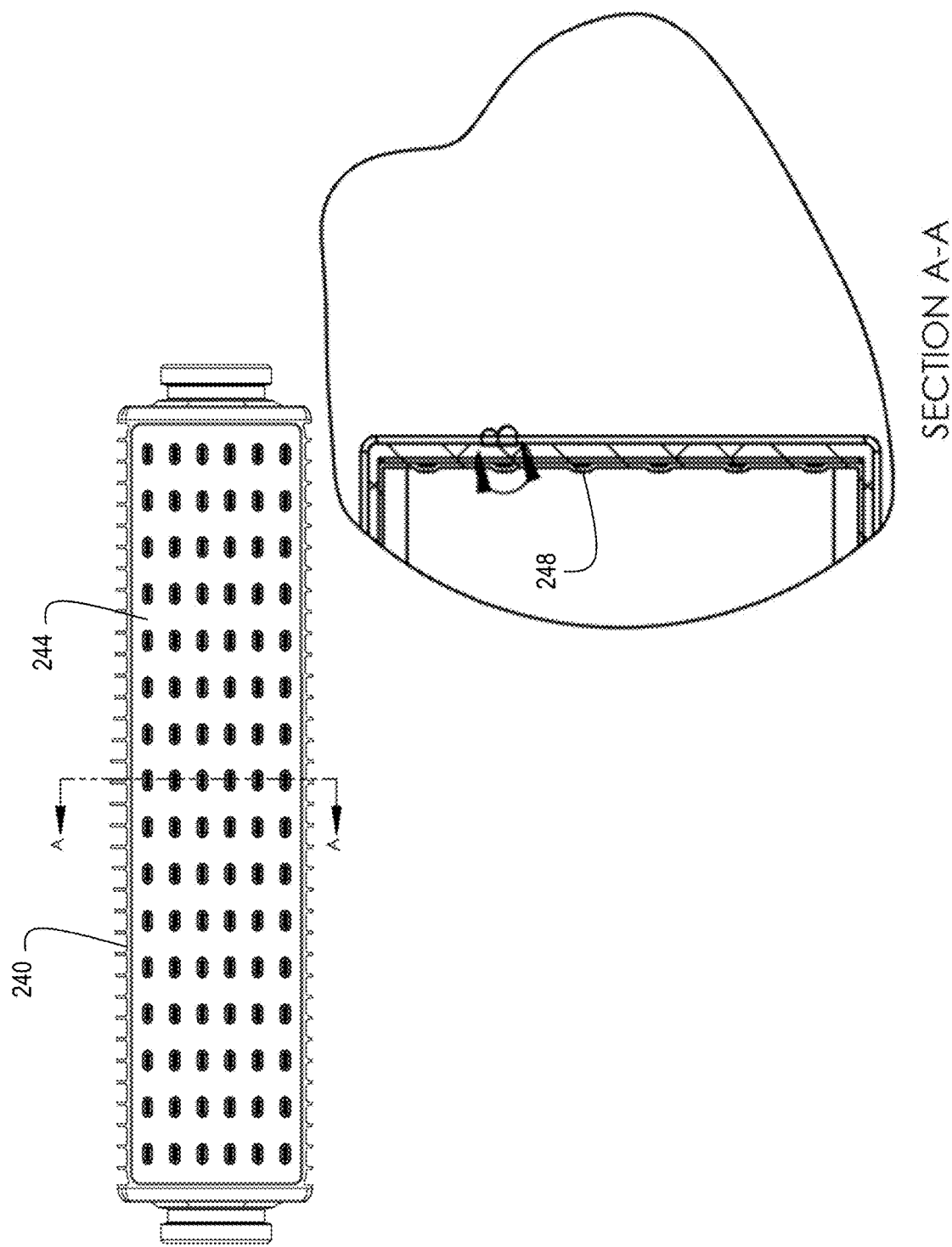
FIG. 25 is a front view of an environmental sealing system for a lighting module according to the present invention.
Figure 26:
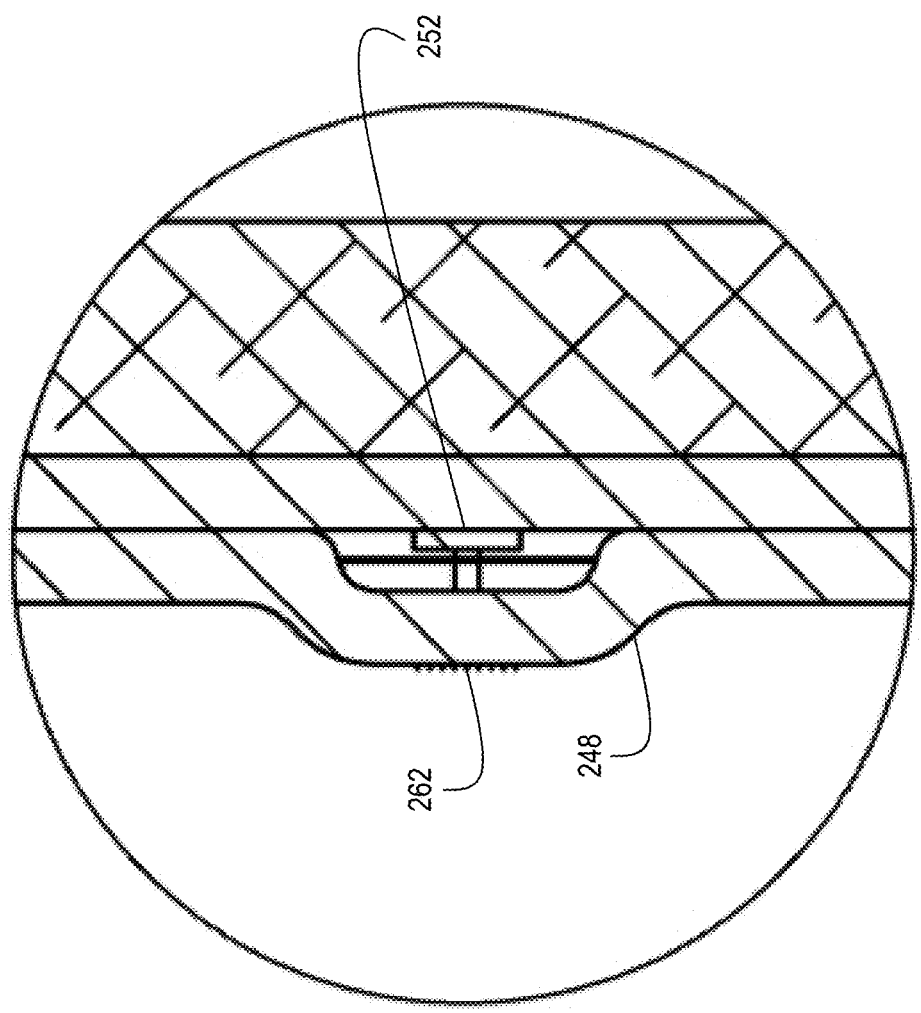
FIG. 26 is a side view of a micro-lens for a lighting module according to the present invention.
Figure 27:
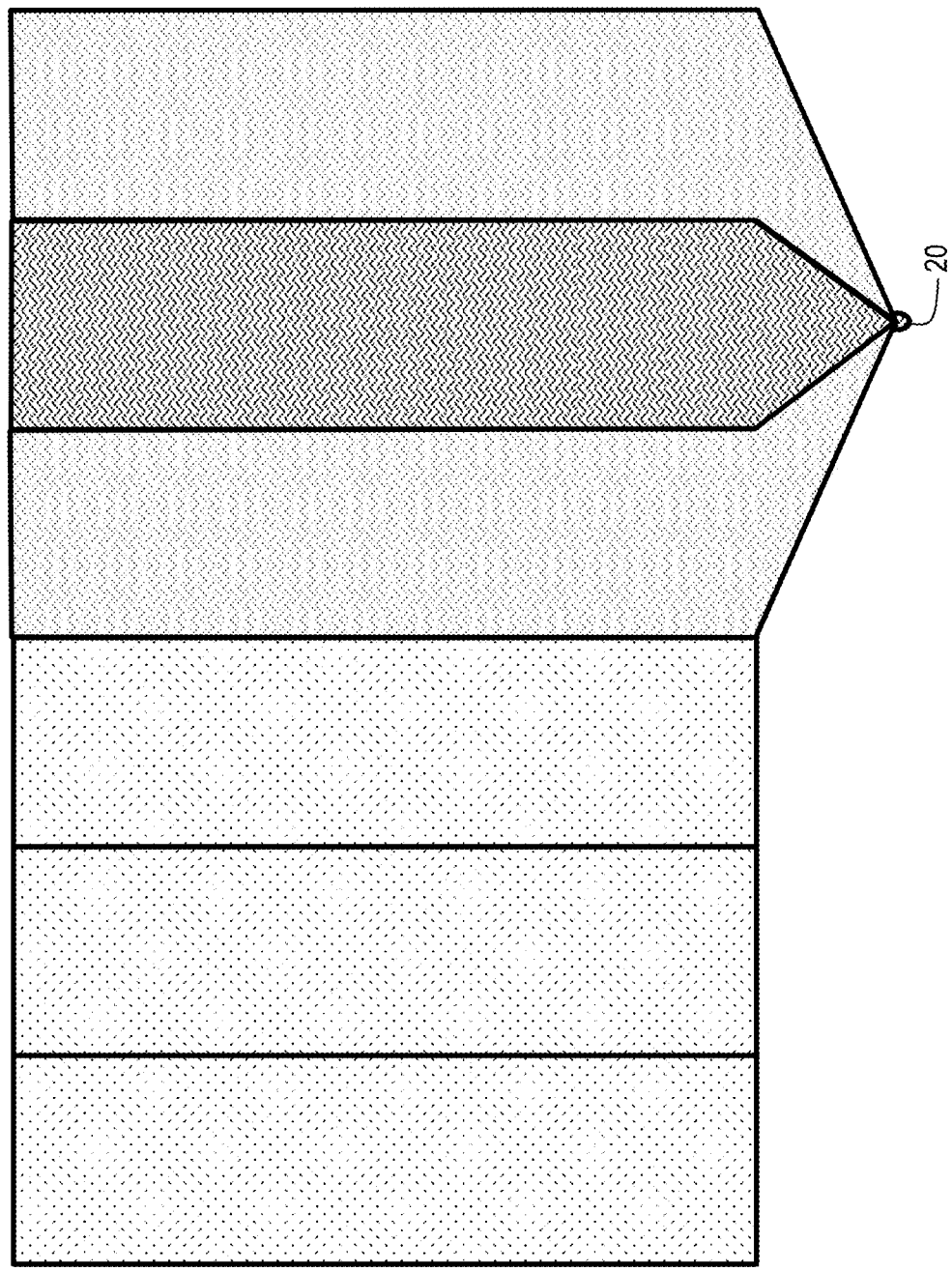
FIG. 27 is a first view of illumination steering using a lens array according to the present invention.
Figure 28:
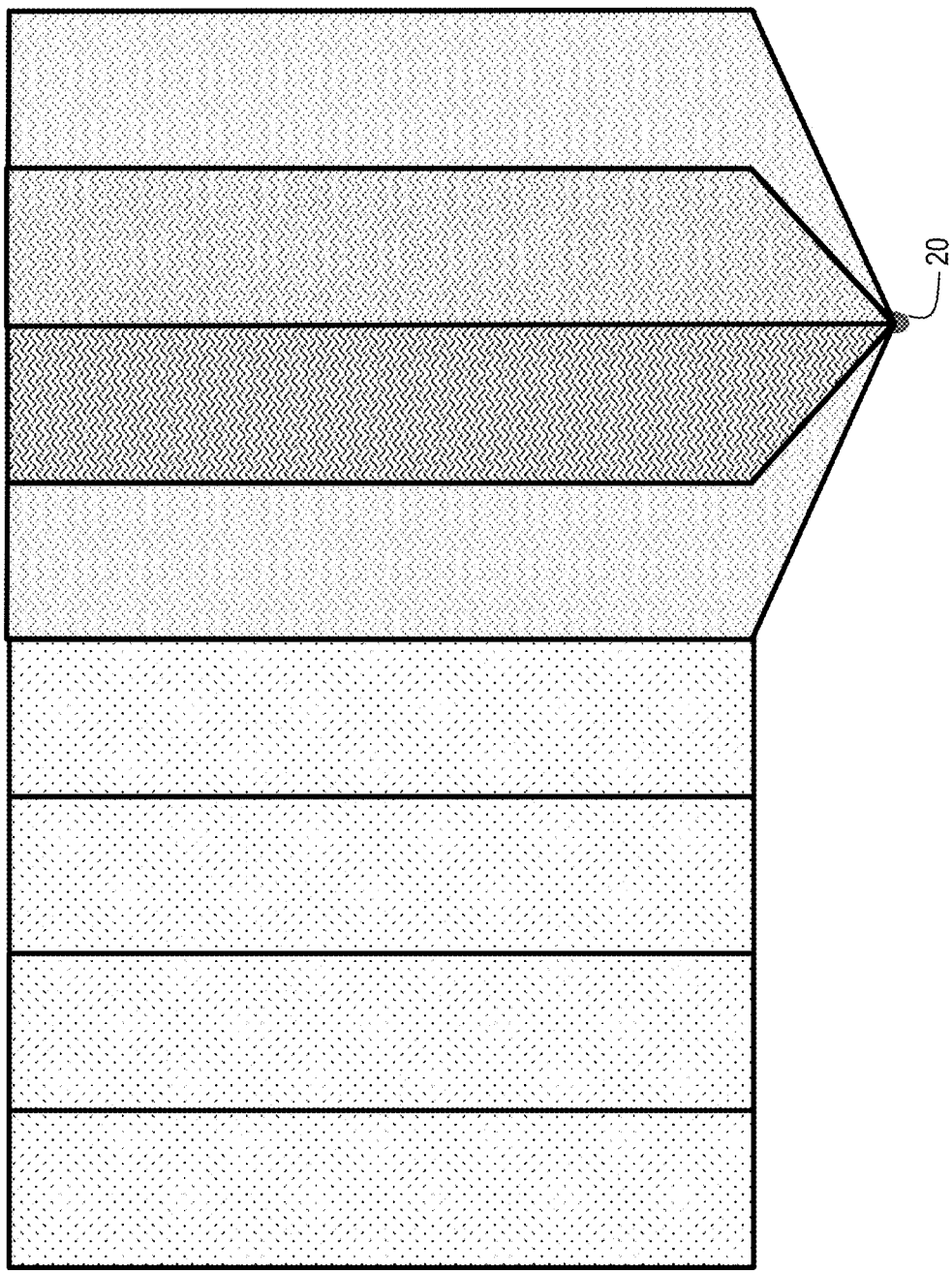
FIG. 28 is a second view of illumination steering using a lens array according to the present invention.
Figure 29:
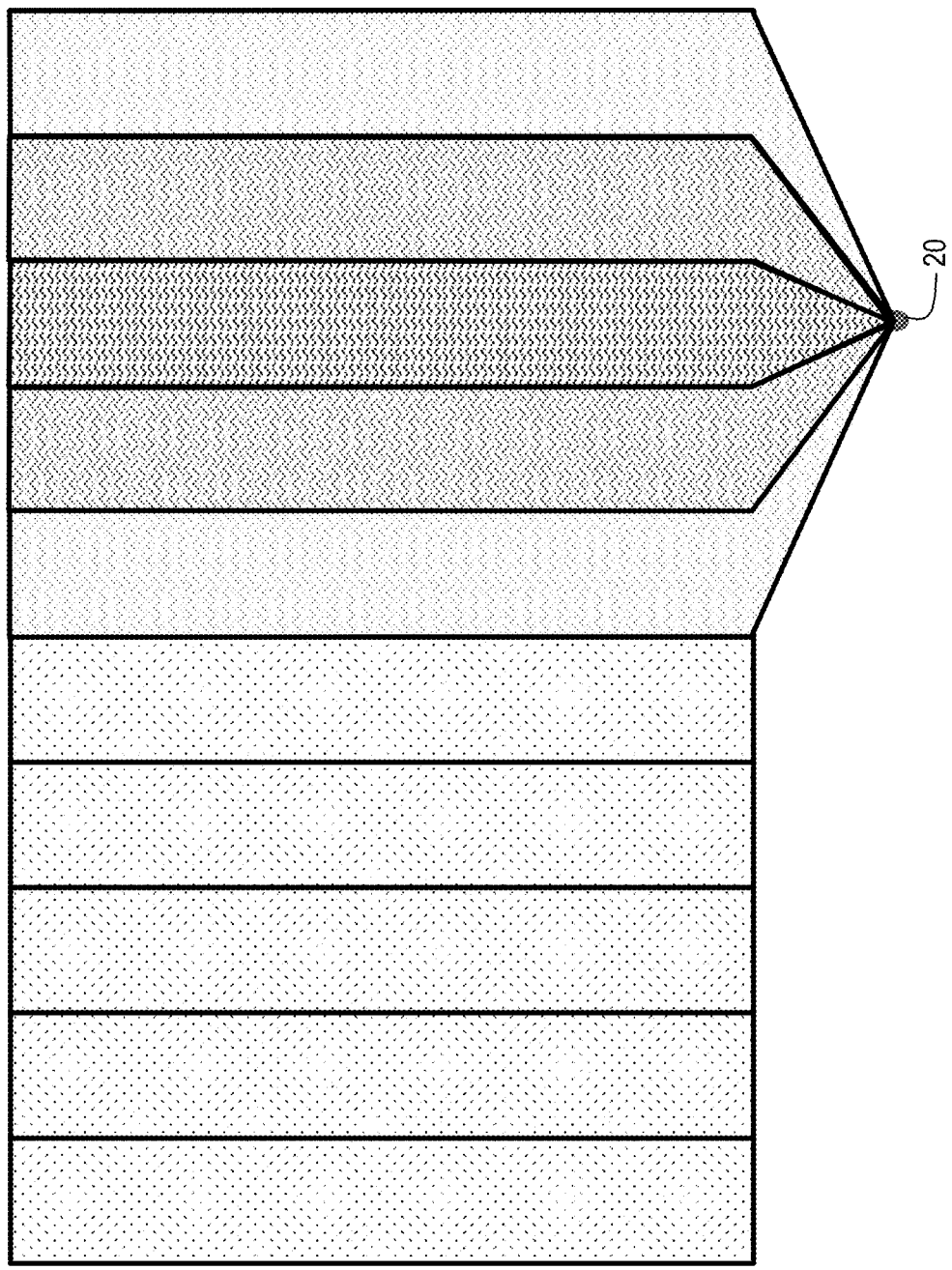
FIG. 29 is a third view of illumination steering using a lens array according to the present invention.

Referring to FIG. 24, lighting module 20 may be constructed using a housing 240 that encloses an asymmetric illumination source 244 and is environmentally sealed prior to attachment of lens array 260. As seen in FIG. 25, housing 240 includes a resilient optical layer 248 positioned over asymmetric illumination source 244 and captured within rectangular opening 242 to seal housing 240 from environmental infiltration. As a result, lens array 260 may be attached or removed from housing 240 in the field, such as to adjust the optical conditioning being provided, without compromising the environmental integrity of housing 240. Optical layer 248 is preferably formed from a moldable optical silicone, such as SILASTIC® MS-1002 moldable silicone and related moldable silicone compounds. As seen in FIG. 26, optical layer 248 may include micro-lenses 262 molded therein and in alignment with each LED set 252 of asymmetric illumination source 244. Optical layer 248 thus performs pre-modulation of the illumination from lighting module 20. Micro-lenses 262 allow for finer optical texturing than with lens array 260 alone. In addition, as lens array 260 does not need to perform as much optical conditioning, lens array 260 can be smaller and thus lighter than otherwise possible.

Figure 30:
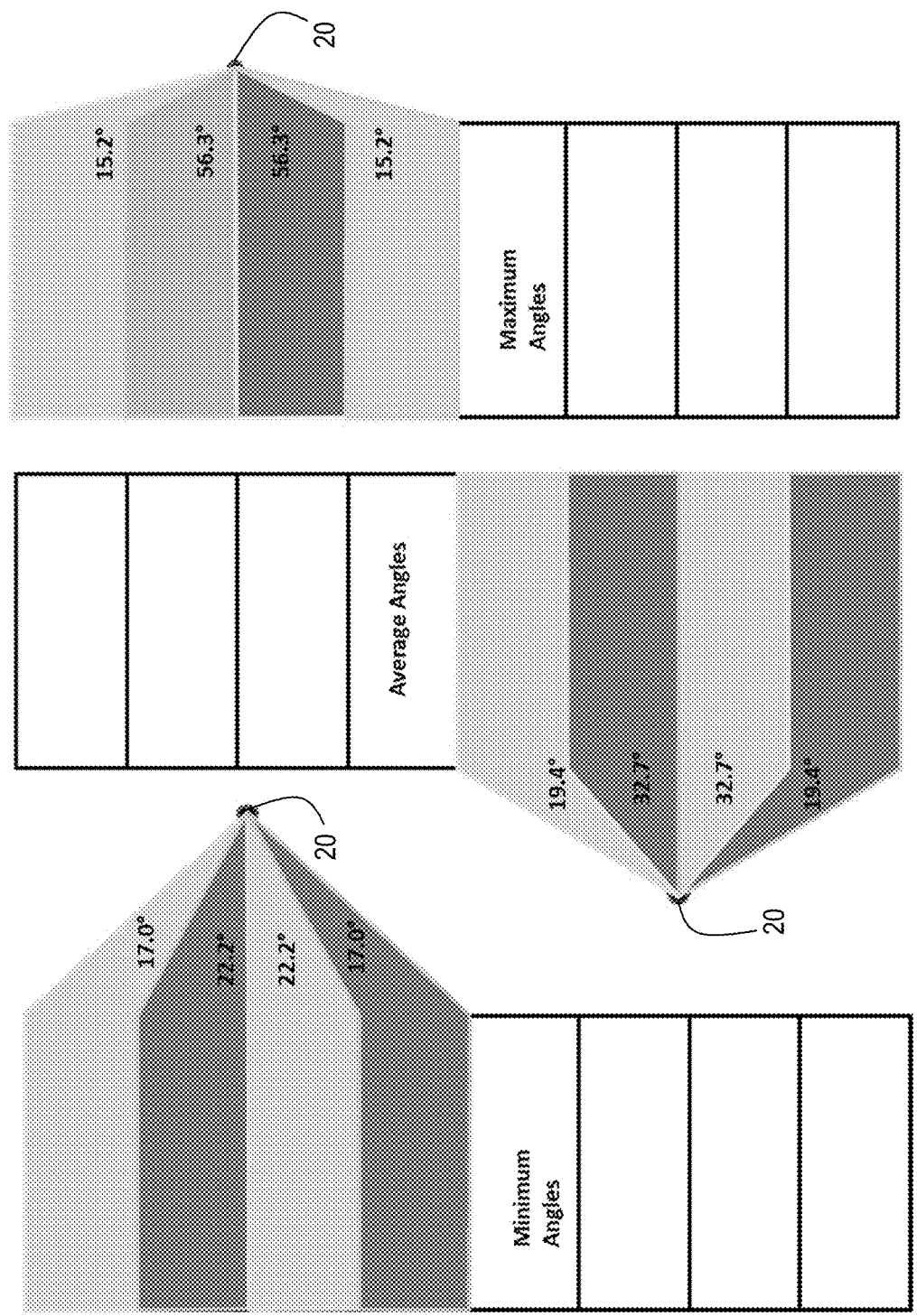
FIG. 30 is a fourth view of illumination steering using a lens array according to the present invention.

Referring to FIGS. 27 through 30, lighting module 20 may be outfitted with lens array 60 configured that steers illumination into three, four, or five different regions. For example, each particular installation may include a different number of support poles 12, so an appropriate lens array 60 distributing illumination into three, four, or five different regions may be used. As is known in the field, illumination from each support pole 12 may need to overlap with illumination for other support poles 12 to provide the desired illumination, reduce or control shadowing, etc. As seen in FIG. 30, lighting module 20 can provide a wide or narrow area of illumination using variously designed lens arrays 60 to steer illumination between a minimum and maximum distribution angle.

As described above, the present invention may be a system, a method, and/or a computer program associated therewith and is described herein with reference to flowcharts and block diagrams of methods and systems. The flowchart and block diagrams illustrate the architecture, functionality, and operation of possible implementations of systems, methods, and computer programs of the present invention. It should be understood that each block of the flowcharts and block diagrams can be implemented by computer readable program instructions in software, firmware, or dedicated analog or digital circuits. These computer readable program instructions may be implemented on the processor of a general purpose computer, a special purpose computer, or other programmable data processing apparatus to produce a machine that implements a part or all of any of the blocks in the flowcharts and block diagrams. Each block in the flowchart or block diagrams may represent a module, segment, or portion of instructions, which comprises one or more executable instructions for implementing the specified logical functions. It should also be noted that each block of the block diagrams and flowchart illustrations, or combinations of blocks in the block diagrams and flowcharts, can be implemented by special purpose hardware-based systems that perform the specified functions or acts or carry out combinations of special purpose hardware and computer instructions.

What is claimed is:

1. An asymmetrically controllable lighting system, comprising:
    a housing extending along a longitudinal axis and having an elongated opening;
    an illumination source positioned in the elongated opening of the housing and having a plurality of rows of light emitting diodes, each of which is coupled to one of a corresponding plurality of independent electrical power pathways; and
    a coupler positioned at one end of the longitudinal axis of the housing and having a plurality of electrical contacts interconnected to plurality of rows of light emitting diodes via each of the independent electrical power pathways.

2. The asymmetrically controllable lighting system of claim 1, wherein the plurality of rows of light emitting diodes extend longitudinally in parallel to the longitudinal axis.

3. The asymmetrically controllable lighting system of claim 2, further comprising an enclosure positioned remotely from the housing and including a plurality of light emitting diode drivers interconnected to the plurality of rows of light emitting diodes by a wiring harness coupled to the plurality of electrical contacts.

4. The asymmetrically controllable lighting system of claim 3, wherein each of the plurality of light emitting diode drivers is configured to control the amount of illumination output by a corresponding one of plurality of rows of light emitting diodes using one of the independent electrical power pathways.

5. The asymmetrically controllable lighting system of claim 4, wherein each of the plurality of light emitting diode drivers includes a local microprocessor responsive to an external command to set the amount of illumination output by the corresponding independently controllable row of light emitting diodes.

6. The asymmetrically controllable lighting system of claim 5, further comprising a central microprocessor having a communication interface programmed to be in wireless communication with a remote host.

7. The asymmetrically controllable lighting system of claim 6, wherein the central microprocessor is programmed to receive a wireless instruction from the remote host regarding the amount of illumination to be output by one of the plurality of rows of light emitting diodes and to send a corresponding digital command to cause the local microprocessor of the corresponding light emitting diode driver for the one of the plurality of rows of light emitting diodes to cause that light emitting diode driver to set the amount of illumination output by the one of the rows of light emitting diodes.

* * * * *